US007569735B2

(12) United States Patent
Ino et al.

(10) Patent No.: US 7,569,735 B2
(45) Date of Patent: Aug. 4, 2009

(54) METHOD FOR PRODUCING ALCOHOLS

(75) Inventors: Yasunori Ino, Kanagawa (JP); Akifumi Yoshida, Kanagawa (JP); Wataru Kuriyama, Kanagawa (JP)

(73) Assignee: Takasago International, Tokyo (JP)

( * ) Notice: Subject to any disclaimer, the term of this patent is extended or adjusted under 35 U.S.C. 154(b) by 0 days.

(21) Appl. No.: 12/076,150

(22) Filed: Mar. 14, 2008

(65) Prior Publication Data

US 2008/0228012 A1 Sep. 18, 2008

(30) Foreign Application Priority Data

| | | |
|---|---|---|
| Mar. 16, 2007 | (JP) | 2007-069201 |
| May 22, 2007 | (JP) | 2007-134905 |
| Oct. 16, 2007 | (JP) | 2007-269229 |

(51) Int. Cl.
*C07C 29/132* (2006.01)
*C07C 29/136* (2006.01)
*C07C 29/88* (2006.01)

(52) U.S. Cl. .......................... 568/814; 568/830; 568/914

(58) Field of Classification Search ................. 568/814, 568/830, 914
See application file for complete search history.

(56) References Cited

FOREIGN PATENT DOCUMENTS

| | | |
|---|---|---|
| JP | 2001-247499 | 9/2001 |
| JP | 2004-238306 | 8/2004 |
| JP | 2004-300131 | 10/2004 |
| JP | 2005-524704 | 8/2005 |
| WO | 11-189600 | 7/1999 |
| WO | WO 2006/106483 A1 | 10/2006 |
| WO | WO 2006/106484 A1 | 10/2006 |

OTHER PUBLICATIONS

Grey, R., et al., "Homogeneous Catalytic Hydrogenation of Carboxylic Acid Esters to Alcohols", J.C.S. Chem. Comm., 1980, pp. 783-784.

Nomura, K., et al., "Direct synthesis of 2-phenylethanol by hydrogenation of methyl phenylacetate using homogeneous ruthenium-phosphine catalysis under low hydrogen pressure", Journal of Molecular Catalysis A: Chemical, 2001, pp. 345-349, vol. 166, Elsevier.

Zhang, J., et al., "Efficient Homogeneous Catalytic Hydrogenation of Esters to Alcohols", Angewandte Chemie Int. Ed., 2006, pp. 1113-1115, vol. 45, Wiley-VCH Verlag GmbH & Co. KGaA, Weinheim.

Greene, T., et al., Protective Groups in Organic Synthesis 2nd Edition, 1991, John Wiley & Sons, Inc.

Inorganic Syntheses, 1970, vol. 12, p. 238.

Inorganic Syntheses, 1970, vol. 17, p. 75.

Kitamura, M., et al., "Asymmetric Hydrogenation of 3-OXO Carboxylates Using BINAP-Ruthenium Complexes: (R)-(-)-Methyl 3-Hydroxybutanoate (Butanoic acid, 3-hydroxy-, methyl ester, (R)-)", Org. Synth., 1993, pp. 1-13.

European Search Report issued in European Patent Application No. EP 08 15 2538, mailed Jul. 24, 2008.

Saudan, L., et al., "Dihydrogen Reduction of Carboxylic Esters to Alcohols under the Catalysis of Homogeneous Ruthenium Complexes: High Efficiency and Unprecedented Chemoselectivity", Angew. Chem. Int. Ed., Aug. 2007, pp. 7473-7476, vol. 46.

Teunissen, H., et al., "Homogeneous ruthenium catalyzed hydrogenation of esters to alcohols", Chem. Commun., Jan. 1998, 1367-1368, vol. 1998.

*Primary Examiner*—Sikarl A Witherspoon
(74) *Attorney, Agent, or Firm*—McDermott Will & Emery LLP

(57) ABSTRACT

A method for producing alcohols which comprises reducing esters or lactones with hydrogen gas in the presence of a catalyst comprising (i) a ruthenium compound, (ii) a monodentate monophosphine or a bidentate bisphosphine, and (iii) an amine. Examples of the catalyst include a ruthenium (Ru) complex represented by the formula: $RuX^1X^2(L_P)_m(L_N)_n$ [$X^1$ and $X^2$ each represent an anionic ligand, $L_P$ represents a phosphine ligand, m is 1 when $L_P$ is bidentate, while m is 2 when $L_P$ is monodentate, $L_N$ represents an amine ligand, and n is 1 when $L_N$ is bidentate, while n is 2 when $L_N$ is monodentate.] and a catalyst comprising an amine and a ruthenium (Ru) complex of the formula: $RuX^1X^2(L_P^1)_r$ [$L_P^1$ represents a monophosphine ligand and r is 3 or 4.].

8 Claims, No Drawings

METHOD FOR PRODUCING ALCOHOLS

BACKGROUND OF THE INVENTION

1. Field of the Invention

The present invention relates to a method for producing alcohols by hydrogen reduction of esters or lactones.

2. Description of the Related Art

Methods for producing alcohols by reduction of esters or lactones are important in chemical synthesis. It is generally considered difficult to reduce an ester or lactone group by catalytic reduction, and methods of using a stoichiometric amount or more of a metal hydride compound such as lithium aluminum hydride have been used frequently. The method by the catalytic hydrogenation, however, is superior from the points of drastic reduction of waste, sustainable chemistry, and safety operation. Therefore, there has been a need for its development. For this reason, there have been many proposals concerning alcohol production by catalytic hydrogenation of esters or lactones, for example, using a homogeneous or heterogeneous catalyst. There are recently more reports on the homogeneous catalyst, because it gives more variety in designing the catalyst than the heterogeneous catalyst.

Methods of producing alcohols by hydrogenation of esters and lactones using a heterogenous catalyst were reported. Meanwhile, JP-A-2001-247499 (Patent Document 1), JP-A-2004-300131 (Patent Document 2), JP-A-2005-524704 (Patent Document 3), J. Chem. Soc. Chem. Commun., 1980, 783 (Non-patent Document 1), J. Mol. Catal. A, 2001, 166, 345-349 (Non-patent Document 2), Angew. Chem. Int. Ed., 2006, 45, 1113 (Non-patent Document 3) and others describe homogenous hydrogenations of esters using a ruthenium complex comprising a ruthenium compound and an organic phosphine compound. WO2006/106483 (Patent Document 4) and WO2006/106484 (Patent Document 5) describe hydrogenations using a ruthenium complex containing a ruthenium compound and a bidentate or tetradentate aminophosphine ligand. Further, JP-A-2004-238306 (Patent Document 6) discloses a homogeneous carbonyl group-hydrogenating method using a ruthenium hydride catalyst.

However, the methods using heterogeneous catalyst demand a severe reaction condition at high temperature and/or high pressure, and thus, have significant limitation on operation, production apparatus and others. In addition, the hydrogenations described in Patent Documents 1 to 3 and Non-patent Documents 1 to 3 are not satisfactory both in yield and catalytic efficiency, and thus, may not be considered to be economically advantageous methods. Alternatively, a fluorine-containing alcohol is used as a solvent in the hydrogenations of ester described in Patent Document 2 and Non-patent Document 1, causing a concern about cost-effectiveness and environment load. Yet alternatively, the method described in Non-patent Document 2, which demands a high temperature of 180 to 200° C., causes a concern about cost-effectiveness and convenience of operation from the industrial viewpoint. Further, 1,4-dioxane, an economically disadvantageous and possibly harmful solvent, is used in the method disclosed in Non-patent Document 3. A ruthenium complex having a ligand containing both phosphorus and nitrogen atoms in the same molecule is used in the methods described in Patent Documents 4 and 5, and thus, it would be more complicated and difficult to prepare the ligand. Hydrogenation of an ester group is considered difficult in the method described in Patent Document 6 (see Example 8).

SUMMARY OF THE INVENTION

Accordingly, an object of the present invention is to provide a method for producing alcohols from esters or lactones easily at high yield and high catalytic efficiency under a relatively milder condition, by use of a catalyst which can be prepared easily.

After intensive studies under the circumstances above, the inventors have found that it is possible to produce alcohols from its corresponding esters or lactones at high yield and high catalytic efficiency by use of a specific ruthenium catalyst and the present invention was completed based on the finding.

The present invention relates to methods for producing alcohols described in the following items [1] to [11].

[1] A method for producing alcohols which comprises reducing esters or lactones with hydrogen gas in the presence of a catalyst comprising the following components (i), (ii) and (iii):
(i) a ruthenium compound;
(ii) a monodentate monophosphine or a bidentate bisphosphine; and
(iii) an amine.

[2] The method for producing alcohols described in item [1], wherein the catalyst is a ruthenium (Ru) complex represented by the following General Formula (1):

$$RuX^1X^2(L_P)_m(L_N)_n \qquad (1)$$

wherein $X^1$ and $X^2$ each represent an anionic ligand; $L_P$ represents a phosphine ligand; m is 1 when $L_P$ is bidentate, while m is 2 when $L_P$ is monodentate; $L_N$ represents an amine ligand; and n is 1 when $L_N$ is bidentate, while n is 2 when $L_N$ is monodentate.

[3] The method for producing alcohols described in item [1], wherein the catalyst is a catalyst comprising an amine and a ruthenium-monophosphine complex represented by the following General Formula (2):

$$RuX^1X^2(L_P^1)_r \qquad (2)$$

wherein $X^1$ and $X^2$ each represent an anionic ligand, $L_P^1$ represents a monophosphine ligand, and r is 3 or 4.

[4] The method for producing alcohols described in item [2], wherein $L_P$ is a bisphosphine ligand and $L_N$ is a diamine ligand in the ruthenium complex represented by General Formula (1).

[5] The method for producing alcohols described in item [2], wherein $X^1$ and $X^2$ are halogen atoms, $L_P$ is a bisphosphine ligand, and $L_N$ is a diamine ligand in the ruthenium complex represented by General Formula (1).

[6] The method for producing alcohols described in item [2], wherein $X^1$ is a hydrogen atom, $X^2$ is $BH_4$, $L_P$ is a bisphosphine ligand, and $L_N$ is a diamine ligand in the ruthenium complex represented by General Formula (1).

[7] The method for producing alcohols described in item [2], wherein $L_P$ is a monophosphine ligand and $L_N$ is a diamine ligand in the ruthenium complex represented by General Formula (1).

[8] The method for producing alcohols described in any one of items [2] to [7], wherein the esters or lactones are reduced further in the presence of an additive or additives.

[9] The method for producing alcohols described in item [8], wherein a mixture of the ruthenium complex represented by General Formula (1) or (2) and the additive or additives previously mixed is used as the catalyst.

[10] The method for producing alcohols described in item [8] or [9], wherein the additive is a base or a reducing agent.

[11] The method for producing alcohols described in item [6], wherein an ester or lactone to be used is an optically active substance, and an alcohol obtained retains an optical purity of 90% or more of that of the ester or lactone to be hydrogen-reduced.

ADVANTAGEOUS EFFECT OF THE INVENTION

According to the production method of the present invention, it is possible to produce alcohols from esters or lactones at high yield and high catalytic efficiency under an industrially advantageous condition of relatively low hydrogen pressure and low reaction temperature. It is also possible to inhibit side reactions such as the reduction of an aromatic ring by lowering the pressure and temperature. Even if a solvent is used, there is no need for use of a solvent that is unfavorable from the points of environment and health. Further, as relatively cheap and easily available reagents are used as the ligand, the method is advantageous from the economical viewpoint. Furthermore, when the ester or lactone to be reduced is an optically active substance, it is possible to reduce it into an alcohol without loss in optical purity, for example, by use of the complex described in item [6] as the catalyst.

DETAILED DESCRIPTION OF THE INVENTION

In the invention, an ester or lactone is used as a substrate of hydrogenation. The examples of the ester to be used as the substrate include aliphatic carboxylate and aromatic carboxylate. The esters may be esters derived from monocarboxylic acids or polycarboxylic acids. These esters and lactones may be substituted with any substituents as long as the substituent does not have adverse effects on the hydrogenation method according to the present invention.

Examples of the esters to be used as the substrates in the invention include alkyl esters of the aliphatic or aromatic carboxylic acid described below with a straight-chain, branched-chain or cyclic alkyl group having 1 to 30 carbon atoms, preferably 1 to 20 carbon atoms, more preferably 1 to 10 carbon atoms, and still more preferably 1 to 5 carbon atoms, such as methyl ester, ethyl ester, propyl ester, butyl ester, hexyl ester, and octyl ester; aryl esters thereof with a monocyclic, polycyclic, or fused-ring aryl group having 6 to 40 carbon atoms, preferably 6 to 30 carbon atoms, more preferably 6 to 20 carbon atoms, and still more preferably 6 to 12 carbon atoms, such as phenyl ester, biphenyl ester and naphthyl ester; and aralkyl esters thereof with an aralkyl group having 7 to 40 carbon atoms, preferably 7 to 20 carbon atoms, and more preferably 7 to 15 carbon atoms, such as benzyl ester and 1-phenethyl ester. Favorable esters include alkyl esters having 1 to 5 carbon atoms such as methyl ester and ethyl ester.

The aliphatic carboxylic acid constituting the esters used as the substrate in the method according to the invention is, for example, a mono- or poly-carboxylic acid having 2 to 30 carbon atoms, preferably 2 to 20 carbon atoms, and more preferably 2 to 15 carbon atoms, which may be substituted. The aliphatic group in the aliphatic carboxylic acid may be linear or cyclic, and also may be saturated or unsaturated. Typical examples thereof include acetic acid, propionic acid, butyric acid, valeric acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, cyclopentanecarboxylic acid, cyclohexanecarboxylic acid, cyclopentenecarboxylic acid, and cyclohexenecarboxylic acid.

These aliphatic carboxylic acids may be substituted with substituents, and examples of the substituents include alkyl groups, alkoxy groups, halogen atoms (fluorine, chlorine, bromine, and iodine), amino groups, aryl groups, heteroaryl groups, aralkyl groups, and a hydroxyl group.

The alkyl group as the substituent on the aliphatic carboxylic acid may be a straight-chain, branched-chain or cyclic alkyl group, and examples thereof include methyl, ethyl, n-propyl, isopropyl, n-butyl, isobutyl, sec-butyl, tert-butyl, n-pentyl, n-hexyl, n-octyl, cyclopropyl, cyclopentyl, and cyclohexyl groups.

The alkoxy group as the substituent on the aliphatic carboxylic acid is, for example, an alkoxy group of a straight-chain, branched-chain or cyclic alkyl group having 1 to 20 carbon atoms, preferably 1 to 15 carbon atoms, and more preferably 1 to 10 carbon atoms (The number of carbons is 3 or more, when cyclic.). Examples thereof include methoxy, ethoxy, n-propoxy, isopropoxy, n-butoxy, isobutoxy, sec-butoxy, tert-butoxy, n-pentyloxy, n-hexyloxy, n-octyloxy, cyclopentyloxy and cyclohexyloxy groups.

Examples of the amino groups as the substituent on the aliphatic carboxylic acid include an amino group; a mono- or di-alkylamino group such as N-methylamino, N,N-dimethylamino, N,N-diethylamino, N-N-diisopropylamino and N-cyclohexylamino groups; a mono- or di-arylamino group such as N-phenylamino, N,N-diphenylamino, N-naphthylamino, and N-naphthyl-N-phenylamino groups; and a mono- or di-aralkylamino group such as N-benzylamino and N,N-dibenzylamino groups. Alternatively, the amino group may be an amino group protected by the common protective group such as that described in Theodora W. Greene and Peter G. M. Wuts, PROTECTING GROUPS IN ORGANIC SYNTHESIS, Second Edition, JOHN WILEY & SONS, INC. 1991. Examples of the protective group include tert-butoxycarbonyl (Boc), benzyloxycarbonyl (Cbz), acetyl (Ac), p-toluenesulfonyl (Ts), and tert-butyldimethylsilyl (TBS).

The aryl group as the substituent on the aliphatic carboxylic acid is, for example, a phenyl, naphthyl, or biphenyl group. The aryl groups may be substituted with the substituents described above such as alkyl groups, alkoxy groups, halogen atoms, and amino groups.

Further, the heteroaryl group as the substituent on the aliphatic carboxylic acid include, for example a 5- to 8-membered, preferably 5- or 6-membered monocyclic heteroaryl group or a polycyclic or fused heteroaryl group, which has 2 to 15 carbon atoms and containing at least one hetero atom, preferably 1 to 3 hetero atoms such as a nitrogen atom, oxygen atom and sulfur atom. Typical examples thereof include furyl, thienyl, pyridyl, pyrimidinyl, pyrazinyl, pyridazinyl, pyrazolyl, imidazolyl, oxazolyl, thiazolyl, benzofuryl, benzothienyl, quinolyl, isoquinolyl, quinoxalinyl, phthalazinyl, quinazolinyl, naphthyridinyl, cinnolinyl, benzimidazolyl, benzoxazolyl, and benzothiazolyl groups.

The aralkyl group as the substituent on the aliphatic carboxylic acid is, for example, a benzyl or 1-phenethyl group.

The hydroxyl group as the substituent on the aliphatic carboxylic acid may be protected by silyl group which is described as common protective group for hydroxyl group in Theodora W. Greene and Peter G. M. Wuts, PROTECTING GROUPS IN ORGANIC SYNTHESIS, Second Edition, JOHN WILEY & SONS, INC. 1991. Examples of the silyl group include trimethyl silyl (TMS), triethylsilyl (TES), triisopropylsilyl (TIPS), tert-butyldimethylsilyl (TBDMS), and tert-butyldiphenyllsilyl (TBDPS).

The aromatic carboxylic acid constituting the esters used as the substrate in the method according to the invention is, for example, an aromatic carboxylic acid having a monocyclic, polycyclic or fused-ring aryl group having 6 to 36 carbon atoms, preferably 6 to 18 carbon atoms, and more preferably 6 to 12 carbon atoms; or an aromatic carboxylic acid having a 3- to 8-membered, preferably 5- to 8-membered monocyclic, polycyclic, or fused-ring heteroaryl group containing 1 to 4 hetero-atoms, preferably 1 to 3 hetero-atoms, more preferably 1 to 2 hetero-atoms such as nitrogen, oxygen and sulfur atoms. Typical examples thereof include benzoic acid, naphthalenecarboxylic acid, pyridinecarboxylic acid, quinolinecarboxylic acid, furancarboxylic acid, and thiophenecarboxylic acid.

The aromatic carboxylic acids may be substituted with the substituents described above such as alkyl groups, alkoxy groups, halogen atoms, amino groups, aryl groups, heteroaryl groups, aralkyl groups, and a hydroxyl group.

On the other hand, examples of the lactones for use in the invention include β-lactones, γ-lactones, and δ-lactones. These lactones may be substituted with the substituents described above such as alkyl groups, alkoxy groups, halogen atoms, amino groups, aryl groups, heteroaryl groups, aralkyl groups, and a hydroxyl group. The lactone may have a bicyclo-ring structure or a ring structure fused with an aromatic ring.

Hereinafter, the catalyst for use in the invention will be described. In the invention, as described above, used is a catalyst comprising the following components (i), (ii) and (iii):

(i) a ruthenium compound;
(ii) a monodentate monophosphine or bidentate bisphosphine; and
(iii) an amine.

As for the components (i), (ii) and (iii), the catalyst may be (a) a mixture of respective three individual compounds; (b) a mixture of a complex consisting of the components (i) and (ii) and an amine of the component (iii); or (c) a complex consisting of the components (i), (ii) and (iii), but the modes (b) and (c) are preferred.

In the mode (c), the complex consisting of the components (i), (ii) and (iii) is, for example, a ruthenium (Ru) complex represented by the following General Formula (1):

$$RuX^1X^2(L_P)_m(L_N)_n \quad (1)$$

wherein, $X^1$ and $X^2$ each represent an anionic ligand; $L_P$ represents a phosphine ligand; m is 1 when $L_P$ is bidentate, while m is 2 when $L_P$ is monodentate; $L_N$ represents an amine ligand; n is 1 when $L_N$ is bidentate, while n is 2 when $L_N$ is monodentate.

In the ruthenium complex represented by General Formula (1), examples of the anionic ligands include a hydrogen atom, a halogen atom, and a $BH_4$ group, an alkoxy group, a hydroxyl group and an acyloxy group.

Examples of the ruthenium complex represented by General Formula (1), wherein $L_P$ is a bisphosphine ligand, include the following complexes:

(A) ruthenium complexes represented by the following General Formula (3):

$$RuX^1X^2(L_P^2)(L_N^2) \quad (3)$$

wherein, $X^1$ and $X^2$ each independently represent a hydrogen atom, a halogen atom, an alkoxy group, a hydroxyl group or an acyloxy group, particularly preferably $X^1$ and $X^2$ being halogen atoms; $L_P^2$ represents a bisphosphine ligand; and $L_N^2$ represents a diamine ligand.

(B) ruthenium complexes represented by the following General Formula (4):

$$Ru(H)(BH_4)(L_P^2)(L_N^2) \quad (4)$$

wherein, $L_P^2$ represents a bisphosphine ligand and $L_N^2$ represents a diamine ligand.

The bisphosphine ligand $L_P^2$ in General Formulae (1), (3) and (4) is, for example, a ligand represented by General Formula (5):

$$R^1R^2P-Q^1-PR^3R^4 \quad (5)$$

wherein, $R^1$, $R^2$, $R^3$ and $R^4$ each independently represent an alkyl group, an aryl group which may be substituted, or a cycloalkyl group which may be substituted; $R^1$ and $R^2$ and/or $R^3$ and $R^4$ may form a ring with a phosphorous atom; $Q^1$ represents an alkylene chain which may be substituted, a cycloalkylene group which may be substituted, a bivalent arylene group which may be substituted, or a ferrocendiyl group which may be substituted.

In the Formula above, the alkyl group represented by $R^1$, $R^2$, $R^3$ or $R^4$ is, for example, a straight- or branched-chain alkyl group, and examples thereof include methyl, ethyl, n-propyl, isopropyl, n-butyl, isobutyl, sec-butyl, tert-butyl, n-pentyl, n-hexyl and n-octyl groups.

In the Formula above, the aryl group in the aryl group which may be substituted by substituents and represented by $R^1$, $R^2$, $R^3$ or $R^4$ is, for example, a monocyclic, polycyclic, or fused-ring aryl group having 6 to 36 carbon atoms, preferably 6 to 18 carbon atoms, and more preferably 6 to 14 carbon atoms. Typical examples thereof include phenyl, naphthyl, anthryl, phenanthryl and biphenyl groups. Examples of the substituents on these aryl groups include alkyl, alkoxy, aryl and heterocyclic groups.

The alkyl group as the substituent on the aryl group is, for example, a straight-chain or branched-chain alkyl group having 1 to 15 carbon atoms, preferably 1 to 10 carbon atoms, and more preferably 1 to 6 carbon atoms. Typical examples thereof include methyl, ethyl, n-propyl, isopropyl, n-butyl, sec-butyl, isobutyl, tert-butyl, n-pentyl, neopentyl and n-hexyl groups.

The alkoxy group as the substituent on the aryl group is, for example, a straight-chain or branched-chain alkoxy group having 1 to 6 carbon atoms. Typical examples thereof include methoxy, ethoxy, n-propoxy, isopropoxy, n-butoxy, sec-butoxy, isobutoxy, tert-butoxy, n-pentyloxy, neopentyloxy and n-hexyloxy groups.

The aryl group may be substituted with other aryl groups. Examples of the aryl groups as the substituent include aryl groups having 6 to 14 carbon atoms, and typical examples thereof include phenyl, naphthyl, anthryl, phenanthryl and biphenyl groups.

The heterocyclic group as the substituent on the aryl group is, for example, an aliphatic heterocyclic group or a heterocyclic aromatic group. Examples of the aliphatic heterocyclic groups include 5- to 8-membered, preferably 5- or 6-membered monocyclic, polycyclic and fused rings having 2 to 14 carbon atoms and also at least one hetero-atom, preferably 1 to 3 hetero atoms such as nitrogen, oxygen and sulfur atoms. Typical examples of the aliphatic heterocyclic groups include 2-oxopyrrolidyl, piperidino, piperadinyl, morpholino, tetrahydrofuryl, tetrahydropyranyl and tetrahydrothienyl groups. On the other hand, examples of the heterocyclic aromatic groups include 5- to 8-membered, preferably 5- or 6-membered monocyclic, polycyclic or fused-ring aromatic heterocyclic (heteroaryl) groups having 2 to 15 carbon atoms and also at least one hetero-atom, preferably 1 to 3 hetero atoms such as nitrogen, oxygen and sulfur atoms. Typical examples thereof include furyl, thienyl, pyridyl, pyrimidinyl, pyrazinyl, pyridazinyl, pyrazolyl, imidazolyl, oxazolyl, thiazolyl, benzofuryl, benzothienyl, quinolyl, isoquinolyl, quinoxalyl, phthalazinyl, quinazolinyl, naphthylidinyl, cinnolinyl, benzimidazolyl, benzoxazolyl and benzothiazolyl groups.

In addition, the cycloalkyl group in the cycloalkyl groups which are represented by $R^1$, $R^2$, $R^3$ and $R^4$ and may be substituted is, for example, a saturated or unsaturated monocyclic, polycyclic or fused-ring cycloalkyl group having 3 to 15 carbon atoms, preferably 3 to 10 carbon atoms, and favorable examples thereof include 5- or 6-membered cycloalkyl groups. Examples of the favorable cycloalkyl groups include cyclopentyl and cyclohexyl groups. These cycloalkyl groups may be substituted at one or more positions thereof, for example, with those described above as the substituents for the aryl group such as alkyl and alkoxy groups.

Examples of the ring that may be formed with $R^1$ and $R^2$ and/or $R^3$ and $R^4$ is a ring formed with a phosphorus atom to which $R^1$, $R^2$, $R^3$ and $R^4$ are bound and an alkylene group having 3 to 10 carbon atoms, preferably a 4-, 5- or 6-membered ring formed with the phosphorous atom and an alkylene group having 3 to 5 carbon atoms. Typical examples thereof include phosphetane, phospholane, phosphane, 2,4-dimethylphosphetane, 2,4-diethylphosphetane, 2,5-dimethylphospholane, 2,5-diethylphospholane, 2,6-dimethylphosphane, and 2,6-diethylphosphane rings. The alkylene group forming the ring may be substituted with various substituents described above.

An alkylene chain in the alkylene chain which may be substituted and is represented by $Q^1$ is, for example, a linear or branched alkyl chain having 1 to 20 carbon atoms, preferably 1 to 10 carbon atoms, and more preferably 1 to 6 carbon atoms. Typical examples thereof include methylene, ethylene, trimethylene, tetramethylene and pentamethylene groups. Examples of the substituents on these methylene chains include alkyl groups having 1 to 4 carbon atoms such as methyl, ethyl, isopropyl, and t-butyl groups, aryl groups, and substituted aryl groups. Examples of substituents on the substituted aryl group include those described above as the substituents for the aforementioned aryl group such as alkyl, aryl and alkoxy groups. The two substituents on the methylene chain may bond each other to form an aliphatic or aromatic ring, and the substituent on the methylene chain and any one of $R^1$, $R^2$, $R^3$ and $R^4$ may bond to each other to form a 5- to 6-membered aliphatic or aromatic ring containing a phosphorus atom, which may be substituted with a methyl group, for example.

The cycloalkylene group which may be substituted and is represented by $Q^1$ is, for example, a bivalent group of a monocyclic, polycyclic or fused-ring cycloalkylene group having 3 to 15 carbon atoms, preferably 3 to 10 carbon atoms, and more preferably 4 to 6, and examples thereof include cyclobutylene, cyclopentylene, and cyclohexylene groups. Examples of the substituents on the cycloalkylene group include alkyl groups having 1 to 4 carbon atoms such as methyl, ethyl, isopropyl and tert-butyl groups.

Bivalent arylene group in the bivalent arylene group which may be substituted and is represented by $Q^1$ is, for example, a bivalent group of a monocyclic, polycyclic, or fused-ring arylene group having 6 to 36 carbon atoms, preferably 6 to 18 carbon atoms, and more preferably 6 to 12 carbon atoms, and examples thereof include phenylene, biphenyldiyl and binaphthalendiyl groups. Examples of the phenylene group include an o- or m-phenylene group, and the phenylene group may be substituted with alkyl groups such as methyl, ethyl, n-propyl, isopropyl, n-butyl, sec-butyl, isobutyl and tert-butyl groups; alkoxy groups such as methoxy, ethoxy, n-propoxy, isopropoxy, n-butoxy, sec-butoxy, isobutoxy and tert-butoxy groups; and a hydroxyl group, an amino group or substituted amino groups. The biphenyldiyl group and the binaphthalendiyl group are preferably those having a 1,1'-biaryl-2,2'-diyl structure. The biphenyldiyl and binaphthalendiyl groups may be substituted with the aforementioned alkyl groups and alkoxy groups; alkylenedioxy groups such as methylenedioxy, ethylenedioxy, and trimethylenedioxy groups; a hydroxyl group; an amino group; or the aforementioned substituted amino groups.

Examples of the substituents on the ferrocendiyl group which may be substituted and is represented by $Q^1$ include the alkyl, alkoxy, alkylenedioxy, hydroxyl, amino and substituted amino groups.

Typical examples of the bisphosphine compounds represented by General Formula (5) include bisdiphenylphosphinomethane, 1,2-bisdiphenylphosphinoethane, 1,3-bisdiphenylphosphinopropane, 1,4-bisdiphenylphosphinobutane, 1,5-bisdiphenylphosphinopentane, 1,2-bisdiphenylphosphinobenzene, 1,2-bis(anisylphenylphosphino)ethane, 1,2-bis(alkylmethylphosphino)ethane, 2,3-bis(diphenylphosphino)butane, 1,2-bis(diphenylphosphino)propane, 2,3-bis(diphenylphosphino)-5-norbornene, 2,3-O-isopropylidene-2,3-dihydroxy-1,4-bis(diphenyl-phosphino)butane, 1-cyclohexyl-1,2-bis(diphenylphosphino)ethane, 1-substitution-3,4-bis(diphenylphosphino)pyrrolidine, 2,4-bis-(diphenylphosphino)pentane, 1,2-bis(substituted phospholano)benzene (DuPHOSs), 1,2-bis(substituted phospholano)ethane (BPEs), 1-((substituted phospholano)-2-(diphenylphosphino)benzene, 1-(bis(3,5-dimethylphenyl)phosphino)-2-(substituted phospholano)benzene, 1-((substituted phospholano)-2-(bis(3-5-di(t-butyl)-4-methoxyphenyl)-phosphino)benzene, 1-((substituted phospholano)-2-(di-naphthalen-1-yl-phosphino)benzene, 2,2'-bis(diphenylphosphino)-1,1'-bicyclopentane, 2,2'-bis(diphenylphosphino)-1,1'-binaphthyl, 2,2'-bis(diphenylphosphino)-1,1'-(5,5',6,6',7,7',8,8'-octahydrobinaphthyl), 2,2'-bis(di-p-tolylphosphino)-1,1'-binaphthyl, 2,2'-bis(di(3,5-dimethylphenyl)phosphino)-1,1'-binaphthyl, 2,2'-bis(diphenylphosphino)-6,6'-dimethyl-1,1'-biphenyl, (4,4'-bi-1,3-benzodioxole)-5,5'-diylbis(diphenylphosphine), (4,4'-bi-1,3-benzodioxole)-5,5'-diylbis[bis(3,5-dimethyl-phenyl)phosphine], (4,4'-bi-1,3-benzodioxole)-5,5'-diylbis[bis[3,5-bis(1,1-dimethylethyl)-4-methoxyphenyl]phosphine], 2,2'-bis(diphenylphosphino)benzophenone, and 2,2'-bis(di(3,5-dimethylphenyl)phosphino)benzophenone. Also included are the bisphosphine compounds represented by the following Formulae:

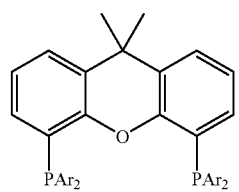 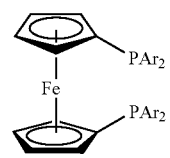

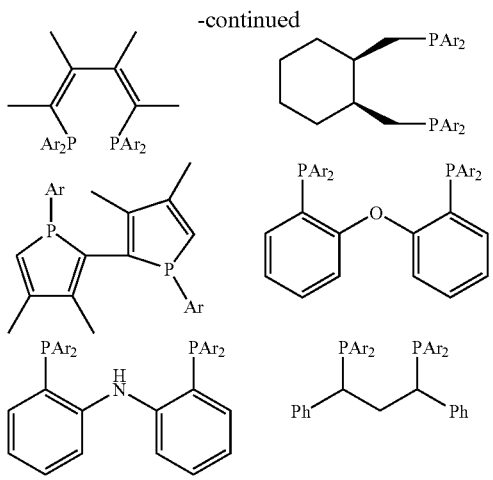

In the Formulae above, Ar represents an aryl group that may be substituted. The aryl group is, for example, a monocyclic, polycyclic or fused-ring aryl group having 6 to 36 carbon atoms, preferably 6 to 18 carbon atoms, and more preferably 6 to 12 carbon atoms. Examples of the substituents include, but are not limited to, alkyl groups having 1 to 4 carbon atoms such as methyl, ethyl, isopropyl and tert-butyl groups. The Ar group is preferably a phenyl, p-tolyl or 3,5-dimethylphenyl group.

Of course, the bisphosphine ligand for use in the invention is not limited to these.

The diamine ligand represented by $L_N^2$ in General Formulae (1), (3) and (4) is, for example, a group represented by the following General Formula (6):

$$R^5R^6N\text{-}Q^2\text{-}NR^7R^8 \quad (6)$$

wherein, $R^5$, $R^6$, $R^7$ and $R^8$ each independently represent a hydrogen atom, an alkyl group which may be substituted, an aryl group which may be substituted, or an alkanesulfonyl or arenesulfonyl group which may be substituted, with proviso one of $R^5$, $R^6$, $R^7$ and $R^8$ is hydrogen atom at least; and $Q^2$ represents an alkylene chain that may be substituted, a cycloalkylene group that may be substituted or an arylene group that may be substituted.

The alkyl group in the alkyl group which may be substituted in General Formula (6) is, for example, a group similar to the alkyl group in $R^1$, $R^2$, $R^3$ and $R^4$, and the substituents are, for example, aryl groups.

An aryl group in the aryl group that may be substituted in General Formula (6) is, for example, an aryl group having 6 to 14 carbon atoms, and typical examples thereof include phenyl, naphthyl, anthryl, phenanthryl and biphenyl groups. The substituents on the aryl group include, but are not limited to, alkyl, alkoxy, aryl, heterocyclic, and mono- or di-substituted amino groups.

The alkanesulfonyl or arenesulfonyl group which may be substituted in General Formula (6) is, for example, a methanesulfonyl, trifluoromethanesulfonyl, benzenesulfonyl or p-toluenesulfonyl group.

The alkylene chain which may be substituted and is represented by $Q^2$ in General Formula (6) is, for example, a group similar to the alkylene chain which may be substituted and is represented by $Q^1$. The cycloalkylene group that may be substituted or the arylene group that may be substituted and is represented by $Q^2$ is, for example, a group similar to that represented by $Q^1$.

Typical examples of the diamine ligands represented by General Formula (6) include diamines such as methylenediamine, ethylenediamine, 1,2-diaminopropane, 1,3-diaminopropane, 2-methyl-1,3-diaminobutane, 1,4-diaminobutane, 2,3-diaminobutane, 1,2-cyclopentanediamine, 1,2-cyclohexanediamine, 1,2-cycloheptanediamine, N-methylethylenediamine, N,N-dimethylethylenediamine, N,N-diethylethylenediamine, N,N-diisopropylethylenediamine, N,N'-dimethylethylenediamine, N,N'-diethylethylenediamine, N,N'-diisopropylethylenediamine, 2,3-dimethyl-2,3-diaminobutane, o-phenylenediamine, 2-(aminomethyl)pyridine, 2-dimethylamino-1-phenylethylamine, 2-diethylamino-1-phenylethylamine, 2-diisopropylamino-1-phenylethylamine, 1,2-diphenylethylenediamine, 1,2-bis(4-methoxyphenyl)ethylenediamine, 1,2-dicyclohexylethylenediamine, 1,2-di(4-N,N-dimethylaminophenyl)ethylenediamine, 1,2-di(4-N,N-diethylaminophenyl)ethylenediamine, 1,2-di(4-N,N-dipropylaminophenyl)ethylenediamine, (N-benzenesulfonyl)-1,2-di(4-N,N-dimethylaminophenyl)-ethylenediamine, (N-p-toluenesulfonyl)-1,2-di(4-N,N-dimethylaminophenyl)-ethylenediamine, (N-methanesulfonyl)-1,2-di(4-N,N-dimethylaminophenyl)-ethylenediamine, (N-trifluoromethanesulfonyl)-1,2-di(4-N,N-dimethylaminophenyl)ethylenediamine, (N-benzenesulfonyl)-1,2-di(4-N,N-diethylaminophenyl)-ethylenediamine, (N-benzenesulfonyl)-1,2-di(4-N,N-dipropylaminophenyl-ethylenediamine, 2,3-dimethyl-1,4-diaminobutane, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphtylethylenediamine, 1-isobutyl-2,2-dinaphtylethylenediamine, 1-isopropyl-2,2-dinaphtylethylenediamine, N,N'-bis(phenylmethyl)-1,2-diphenyl-1,2-ethylenediamine, N,N'-bis(mesitylmethyl)-1,2-diphenyl-1,2-ethylenediamine, and N,N'-bis(naphthylmethyl)-1,2-diphenyl-1,2-ethylene-diamine. Also included are the diamine compounds represented by the following Formulae:

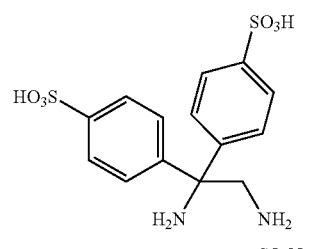

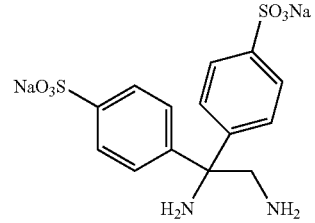

-continued

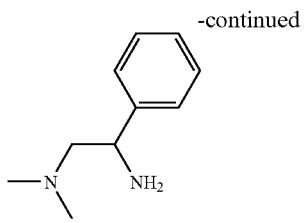

Of course, the diamine ligands for use in the invention are not limited thereto.

The halogen atom represented by $X^1$ or $X^2$ in General Formula (3) is, for example, a chlorine, bromine or iodine atom; and the alkoxy group is, for example, a straight-chain or branched-chain alkoxy group having 1 to 8 carbon atoms, such as methoxy, ethoxy, n-propoxy, isopropoxy, n-butoxy, isobutoxy, sec-butoxy, tert-butoxy, n-pentyloxy, neopentyloxy, n-hexyloxy, n-heptyloxy, or n-octyloxy group.

The acyloxy group represented by $X^1$ or $X^2$ in General Formula (3) is, for example, a group represented by $R_nCO_2$. The group $R''$ in the acyloxy group $R''CO_2$ is, for example, a hydrogen atom, an alkyl group that may be substituted and has 1 to 3 carbon atoms, or a phenyl or naphthyl group that may be substituted. Examples of the substituents on the alkyl group that may be substituted and have 1 to 3 carbon atoms include alkyl groups having 1 to 4 carbon atoms and halogen atoms. Examples of the alkyl groups that may be substituted and have 1 to 3 carbon atoms include methyl, ethyl, propyl, tert-butyl, trifluoromethyl and other groups. Examples of the substituents on the phenyl or naphthyl group that may be substituted include alkyl groups such as methyl, ethyl and n-propyl groups; alkoxy groups such as methoxy, ethoxy and propoxy groups; and halogen atoms such as chlorine and bromine.

Examples of the ruthenium compounds used as a starting material for synthesizing the ruthenium complex according to the invention represented by General Formula (1), (3) or (4) include inorganic ruthenium compounds such as ruthenium halides, for example, $RuCl_3$ hydrate, $RuBr_3$ hydrate, and $RuI_3$ hydrate; $RuCl_2(DMSO)_4$, $[Ru(cod)Cl_2]n$, $[Ru(nbd)Cl_2]n$, $(cod)Ru(\eta^2-O_2CCF_3)_2$, $(cod)Ru(\eta^3-methallyl)_2$, $Ru_2(CO)_6$ $(C_8H_8)$, $RuCl(CO)_3(C_3H_5)$, $Ru(C_5H_5)_2$, $Ru(C_5H_5)$ $(CH_3COC_5H_4)$, $Ru(C_5H_5)(C_5H_4CH_3)$, $[Ru(benzene)Cl_2]_2$, $[Ru(benzene)Br_2]_2$, $[Ru(benzene)I_2]_2$, $[Ru(p-cymene)Cl_2]_2$, $[Ru(p-cymene)Br_2]_2$, $[Ru(p-cymene)I_2]_2$, $[Ru(mesitylene)Cl_2]_2$, $[Ru(mesitylene)Br_2]_2$, $[Ru(mesitylene)I_2]_2$, $[Ru(hexamethylbenzene)Cl_2]_2$, $[Ru(hexamethylbenzene)Br_2]_2$, $[Ru(hexamethylbenzene)I_2]_2$, $RuCl_2(PPh_3)_3$, $RuBr_2(PPh_3)_3$, $RuI_2(PPh_3)_3$, $RuH_2(PPh_3)_4$, $RuH_4(PPh_3)_3$, $RuH_2(N_2)(PPh_3)_3$, and $RuClH(PPh_3)_3$. In the examples above, DMSO represents dimethylsulfoxide; cod, 1,5-cyclooctadiene; nbd, norbornadiene; Ac, acetyl; and Ph, phenyl (the same shall apply hereinafter).

The complex represented by General Formula (3) can be prepared, for example, by the method described in JP-A-11-189600. By the method, for example, a ruthenium compound is first allowed to react with a phosphine ligand in a solvent, and then, the compound obtained is allowed to react with an amine ligand. More specifically, for example, when a ruthenium halide is used as the ruthenium compound, the reaction between the ruthenium halide and the phosphine ligand is carried out in an aromatic hydrocarbon solvent such as toluene or xylene, an aliphatic hydrocarbon solvent such as pentane or hexane, a halogen-containing hydrocarbon solvent such as methylene chloride, an ether solvent such as ether or tetrahydrofuran, an alcohol solvent such as methanol, ethanol, 2-propanol, butanol or benzyl alcohol, a heteroatom-containing organic solvent such as acetonitrile, DMF (N,N-dimethylformamide), N-methylpyrrolidone, or DMSO, or a mixed solvent of them at a reaction temperature in the range of −100° C. to 200° C., to give a phosphine-ruthenium halide complex. Subsequently, the reaction between the phosphine-ruthenium halide complex obtained and the amine ligand is carried out in an aromatic hydrocarbon solvent such as toluene or xylene, an aliphatic hydrocarbon solvent such as pentane or hexane, a halogen-containing hydrocarbon solvent such as methylene chloride, an ether solvent such as ether or tetrahydrofuran, an alcohol solvent such as methanol, ethanol, 2-propanol, butanol, or benzyl alcohol, or a heteroatom-containing organic solvent such as acetonitrile, DMF, N-methylpyrrolidone or DMSO at a reaction temperature in the range of −100° C. to 200° C., to give an amine-phosphine-ruthenium halide complex. However, the production method for the ruthenium complex according to the invention represented by General Formula (3) is not limited thereto.

Alternatively, the ruthenium complex represented by General Formula (4) can be prepared, for example, by the method described in JP-A-2004-238306. By the method, for example, a ruthenium compound is allowed to react with a bisphosphine ligand in a solvent, and then, the compound obtained is allowed to react with a diamine ligand and further with a metal borohydride compound. The reaction of the starting material ruthenium compound and the bisphosphine ligand is carried out in an aliphatic or aromatic hydrocarbon solvent such as pentane, hexane, heptane, toluene or xylene, a halogenated hydrocarbon solvent such as methylene chloride, an ether solvent such as diethyl ether or tetrahydrofuran, an alcohol solvent such as methanol, ethanol, isopropanol, butanol or benzyl alcohol, an organic solvent such as acetonitrile, N,N-dimethylacetamide, N,N-dimethylformamide, N-methylpyrrolidone or dimethylsulfoxide, or a mixed solvent of them at a reaction temperature in the range of −100° C. to 200° C., to give a ruthenium-bisphosphine complex. The reaction between the ruthenium-bisphosphine complex obtained and the diamine ligand is carried out in an aliphatic or aromatic hydrocarbon solvent such as pentane, hexane, heptane, toluene or xylene, a halogenated hydrocarbon solvent such as methylene chloride, an ether solvent such as diethyl ether or tetrahydrofuran, an alcohol solvent such as methanol, ethanol, isopropanol, butanol, or benzyl alcohol, or an organic solvent such as acetonitrile, N,N-dimethylacetamide, N,N-dimethylformamide, N-methylpyrrolidone or dimethylsulfoxide at a reaction temperature in the range of −100° C. to 200° C., to give a ruthenium-bisphosphine-diamine complex.

hydridation of the ruthenium-bisphosphine-diamine complex thus obtained with a metal borohydride compound gives a ruthenium hydride complex represented by General Formula (2). Specifically, the ruthenium-bisphosphine-diamine complex is hydridated in reaction with a metal borohydride compound such as sodium borohydride or potassium borohydride in an organic solvent, for example, in an aliphatic or aromatic hydrocarbon solvent such as pentane, hexane, heptane, toluene or xylene, a halogenated hydrocarbon solvent such as methylene chloride, an ether solvent such as diethyl ether or tetrahydrofuran, or an alcoholic solvent such as methanol, ethanol, isopropanol, butanol or benzyl alcohol, or a mixed solvent of them at a reaction temperature in the range of −100° C. to 200° C., to give a ruthenium hydride complex represented by General Formula (4). Alternatively, the ruthenium-bisphosphine complex may be first converted to a ruthenium-bisphosphine-hydride complex, and then to a ruthenium hydride complex represented by General Formula (4) in reaction with a diamine.

The complex represented by General Formula (3) or (4) is not limited to one diastereomer and may be a cis isomer, a trans isomer, or a cis and trans mixture.

Examples of the ruthenium complexes wherein $L_P$ in the ruthenium complex represented by General Formula (1) is a monophosphine ligand include the followings:

(C) ruthenium complexes represented by the following General Formula (7):

$$RuX^1X^2(L_P^1)_2(L_N^2) \quad (7)$$

wherein, $X^1$ and $X^2$ each represent an anionic ligand; $L_P^1$ represents a monophosphine ligand; and $L_N^2$ represents a diamine ligand.

The monophosphine ligand represented by $L_P^1$ in General Formula (7) is, for example, a monophosphine represented by the following General Formula (8):

$$R^9R^{10}R^{11}P \quad (8)$$

wherein, $R^9$, $R^{10}$ and $R^{11}$ each independently represent an alkyl group, an alkoxy group, an aryl group which may be substituted, an aryloxy group which may be substituted, or a cycloalkyl group which may be substituted.

In the Formula above, the alkyl group represented by $R^9$, $R^{10}$ and $R^{11}$ is, for example, a straight- or branched-chain alkyl group having 1 to 20 carbon atoms, preferably 1 to 15 carbon atoms, and more preferably 1 to 10 carbon atoms. Typical favorable examples of the alkyl groups include methyl, ethyl, n-propyl, isopropyl, n-butyl, isobutyl, sec-butyl, tert-butyl, n-pentyl, n-hexyl and n-octyl groups.

In the Formula above, the alkoxy group represented by $R^9$, $R^{10}$ or $R^{11}$ is, for example, an alkoxy group of a straight-chain or branched-chain or cyclic alkyl group having 1 to 20 carbon atoms, preferably 1 to 15 carbon atoms, and more preferably 1 to 10 carbon atoms (the number of carbons is 3 or more when a cyclic group). Typical favorable examples of the alkoxy groups include methoxy, ethoxy, n-propoxy, isopropoxy, n-butoxy, isobutoxy, sec-butoxy, tert-butoxy, n-pentyloxy, n-hexyloxy, n-octyloxy, cyclopentyloxy, and cyclohexyloxy groups.

In the Formula above, the aryl group in the aryl group which may be substituted and is represented by $R^9$, $R^{10}$ or $R^{11}$ is, for example, an aryl group having 6 to 14 carbon atoms, and typical examples thereof include phenyl, naphthyl, anthryl, phenanthryl, biphenyl and furyl groups. The substituents on the aryl groups include alkyl and alkoxy groups, halogen atoms (fluorine, chlorine, bromine, and iodine), and aryl groups.

The alkyl group as the substituent on the aryl group is, for example, a straight-chain or branched-chain alkyl group having 1 to 15 carbon atoms, preferably 1 to 10 carbon atoms, and more preferably 1 to 6 carbon atoms. Typical examples thereof include methyl, ethyl, n-propyl, isopropyl, n-butyl, sec-butyl, isobutyl, tert-butyl, n-pentyl, neopentyl, and n-hexyl groups.

The alkoxy group as the substituent on the aryl group is, for example, a straight-chain or branched-chain alkoxy group having 1 to 6 carbon atoms, and typical examples thereof include methoxy, ethoxy, n-propoxy, isopropoxy, n-butoxy, sec-butoxy, isobutoxy, tert-butoxy, n-pentyloxy, neopentyloxy and n-hexyloxy groups.

The aryl group as the substituent on the aryl group is, for example, an aryl group having 6to 14 carbon atoms, and typical examples thereof include phenyl, naphthyl, anthryl, phenanthryl, biphenyl and furyl groups.

The aryloxy group in the aryloxy group which may be substituted and is represented by $R^9$, $R^{10}$ or $R^1$ is, for example, an aryloxy group having 6 to 14 carbon atoms, and typical examples thereof include phenoxy, naphthyloxy, anthryloxy, phenanthryloxy and biphenyl groups. The substituents on the aryloxy groups include the alkyl groups, alkoxy groups and halogen atoms described above.

The cycloalkyl group in the cycloalkyl group which may be substituted and is represented by $R^9$, $R^{10}$ and $R^{11}$ is, for example, a 5- or 6-membered cycloalkyl group, and favorable examples thereof include cyclopentyl and cyclohexyl groups. The cycloalkyl group may be substituted with one or more substituents such as the alkyl or alkoxy groups described above as the substituents for the aryl group.

Typical examples of the monophosphines represented by General Formula (8) described above include triphenylphosphine [PPh$_3$], tri(4-methylphenyl)phosphine, tri(3-methylphenyl)phosphine, tri(2-methylphenyl)phosphine, tris(4-trifluoromethylphenyl)phosphine, tri(4-methoxyphenyl) phosphine, tri(3-methoxyphenyl)phosphine, tri(2-methoxyphenyl)phosphine, tris(3,5-dimethylphenyl) phosphine, tris(3,5-dimethoxyphenyl)phosphine, tris(3,5-dimethyl-4-methoxyphenyl)phosphine, tris[3,5-bis(1,1-dimethylethyl)-4-methoxyphenyl]phosphine, tri(4-fluorophenyl)phosphine, tris(3,5-difluorophenyl)phosphine, tri(4-chlorophenyl)phosphine, tris(3,5-dichlorophenyl)phosphine, tri(1-naphthyl)phosphine, trimethylphosphine[PMe$_3$], tris(trifluoromethyl)phosphine, triethylphosphine, tri-n-propylphosphine, triisopropylphosphine, tri-n-butylphosphine, tri-t-butylphosphine, tripentylphosphine, tri-n-hexylphosphine, tri-n-heptylphosphine, trioctylphosphine, tricyclopentylphosphine, tricyclohexylphosphine, methyldiphenylphosphine, cyclohexylmethylphenylphosphine, and dicyclohexylphenylphosphine.

The anionic ligand represented by $X^1$ or $X^2$ in General Formula (7) above is, for example, a halogen atom, an alkoxy group or an acyloxy group. The diamine ligand represented by $L_N^2$ is a ligand similar to that described in General Formula (3) and (4).

Examples of the ruthenium compounds used as the starting material for preparation of the ruthenium complex for use in the invention represented by General Formula (7) include compounds similar to those used in the synthesis of the ruthenium complex represented by General Formula (3), including inorganic ruthenium compounds such as ruthenium halides of RuCl$_3$ hydrate, RuBr$_3$ hydrate, and RuI$_3$ hydrate; RuCl$_2$ (DMSO)$_4$, [Ru(cod)Cl$_2$]n, [Ru(nbd)Cl$_2$]n, [Ru(benzene)Cl$_2$]$_2$, [Ru(benzene)Br$_2$]$_2$, [Ru(benzene)I$_2$]$_2$, [Ru(p-cymene)Cl$_2$]$_2$, [Ru(p-cymene)Br$_2$]$_2$, [Ru(p-cymene)I$_2$]$_2$, [Ru(mesitylene) Cl$_2$]$_2$, [Ru(mesitylene)Br$_2$]$_2$, [Ru(mesitylene)I$_2$]$_2$, [Ru (hexamethylbenzene)Cl$_2$]$_2$, [Ru(hexamethylbenzene)Br$_2$]$_2$, and [Ru(hexamethylbenzene)I$_2$]$_2$. The complex represented by the General Formula (2) described above may also be used as the starting material for the synthesis of the ruthenium complex represented by General Formula (7).

Similarly to the ruthenium complex represented by General Formula (3), the ruthenium complex represented by General Formula (7) can be prepared, for example, by the method described in JP-A-11-189600. By the method, for example, a ruthenium compound is first allowed to react with a monophosphine ligand in a solvent, and the compound obtained is allowed to react with an amine ligand. More specifically, for example, when a ruthenium halide is used as the ruthenium compound, the reaction between the ruthenium halide and the phosphine ligand is carried out in an aromatic hydrocarbon solvent such as toluene or xylene, an aliphatic hydrocarbon solvent such as pentane or hexane, a halogen-containing hydrocarbon solvent such as methylene chloride, an ether solvent such as ether or tetrahydrofuran, an alcohol solvent such as methanol, ethanol, 2-propanol, butanol, or benzyl alcohol, a heteroatom-containing organic solvent such as acetonitrile, DMF (N,N-dimethylformamide), N-methylpyrrolidone or DMSO, or a mixed solvent of them at a suitable reaction temperature, to give a phosphine-ruthenium halide complex. The subsequent reaction between the phosphine-ruthenium halide complex obtained and the amine ligand is carried out in an aromatic hydrocarbon solvent such as toluene or xylene, an aliphatic hydrocarbon solvent such as pentane or hexane, a halogen-containing hydrocarbon solvent such as methylene chloride, an ether solvent such as ether or tetrahydrofuran, an alcohol solvent such as methanol, ethanol, 2-propanol, butanol or benzyl alcohol, a heteroatom-containing organic solvent such as acetonitrile, DMF, N-methylpyrrolidone or DMSO, or a mixed solvent of them at a suitable reaction temperature to give a ruthenium complex represented by General Formula (7). However, the method for producing the ruthenium complex represented by General Formula (7) of the invention is not limited to the method above.

The ruthenium complex represented by General Formula (7) is not limited to one diastereomer and may be a cis isomer, a trans isomer, or a cis and trans mixture.

Although diamine ligands are exemplified as the amine ligands for the ruthenium complex represented by General Formula (1) above, the amine ligand may be a monodentate monoamine ligand. Therefore, the amines for use in the invention include monodentate amines (monoamines and monoimines) and bidentate amines (diamines, diimines and iminoamines). Among them preferable are the bidentate amines described above. Examples of the monoamines, monoimines, diimines and iminoamines in the monodentate amines and bidentate amines include the compounds represented by the following Formulae (A) to (F):

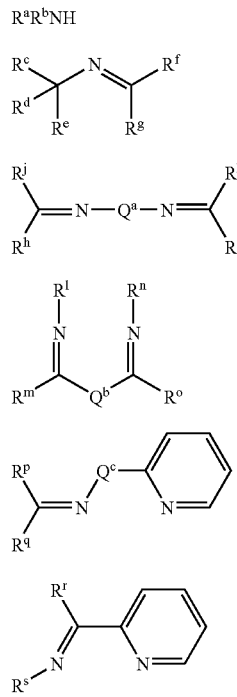

wherein, $R^a$ to $R^s$ each independently represent an alkyl group which may be substituted, an aryl group which may be substituted, or an aralkyl group which may be substituted; $Q^a$, $Q^b$ and $Q^c$ each independently represent an alkylene chain which may be substituted, a cycloalkylene group which may be substituted, or an arylene group which may be substituted; and $R^a$ and $R^b$, $R^c$ and $R^d$, $R^e$ and $R^f$, $R^h$ and $R^i$, $R^j$ and $R^k$, and $R^p$ and $R^q$ each may form an aliphatic ring.

The diamine, the bidentate amine favorably used in the present invention, is preferably a diamine that may be substituted, for example a diamine represented by General Formula (6) above, i.e., the diamine ligand in the ruthenium complex of General Formula (1), (3) or (4) above. Among the diamines represented by General Formula (6), preferred are diamines in which at least one of the groups $R^5$, $R^6$, $R^7$ and $R^8$ is a hydrogen atom.

Examples of the bidentate imine include a diimine represented by Formula (C) that is prepared from a diamine and a ketone or aldehyde; a diimine represented by Formula (D) that is prepared from a diketone, ketoaldehyde or dialdehyde and an amine; and an imine (iminoamine) represented by Formula (E) or (F) that is prepared from an amine and a ketone or aldehyde. Typical examples of the diimines or iminoamines include the followings:

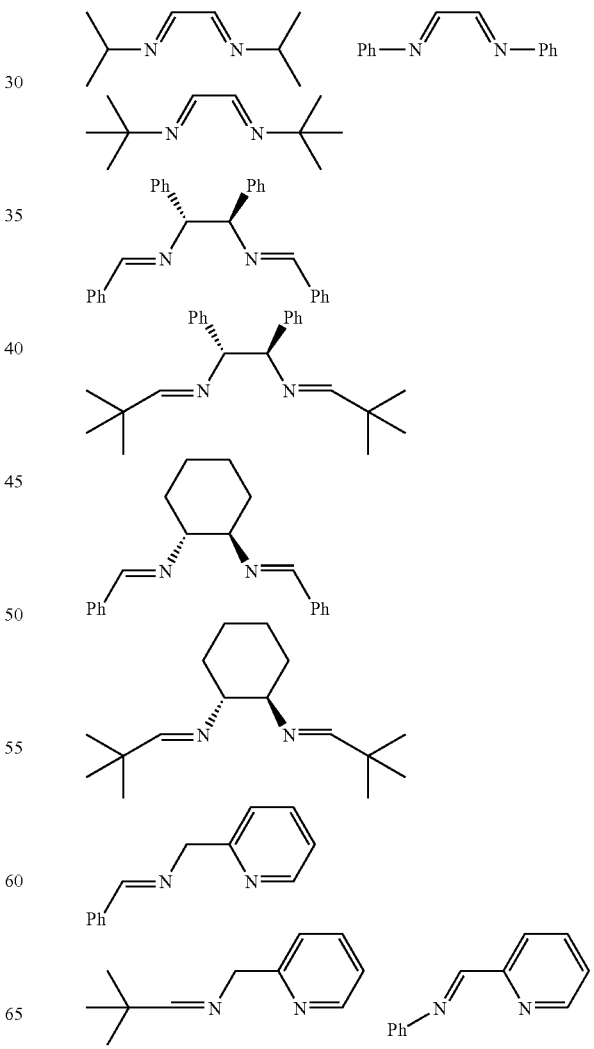

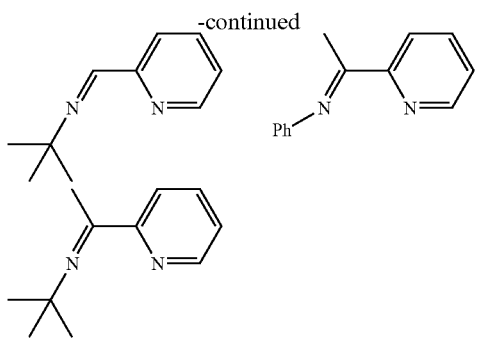

Hereinafter, the catalyst in the mode (b), i.e., a catalyst comprising a complex of components (i) and (ii) and an amine of component (iii), will be described. The complex of components (i) and (ii) is, for example, the following ruthenium complex.

(D) ruthenium complexes represented by the following General Formula (2):

$$RuX^1X^2(L_P^1)_r \quad (2)$$

wherein, $X^1$ and $X^2$ each represent an anionic ligand; $L_P^1$ represents a monophosphine ligand; and r is 3 or 4.

In General Formula (2), there is exemplified the same as those described in General Formulae (1), (3), (4) and (7) as the anionic ligands represented by $X^1$ and $X^2$ and the monophosphine ligand represented by $L_P^1$. In addition, the starting ruthenium compound for synthesis of the complex represented by General Formula (2) is also the same as that described in General Formulae (1), (3), (4) and (7).

The ruthenium complex represented by General Formula (2) is, for example, $RuCl_2(PPh_3)_3$, $RuBr_2(PPh_3)_3$, $RuI_2(PPh_3)_3$, $RuH_2(PPh_3)_4$, $RuH_4(PPh_3)_3$, or $RuClH(PPh_3)_3$ when triphenylphosphine is used as the monophosphine; and $RuCl_2(PMe_3)_3$ when trimethylphosphine is used as the monophosphine. Other ruthenium complex such as $RuCl_2(PCy_3)_3$, $RuCl_2(P(n-Bu)_3)_3$, $RuCl_2(P(t-Bu)_3)_3$, or $RuCl_2(P(4-MeO-C_6H_4)_3)_3$ can also be used. However, the monophosphine is of course not limited thereto. In the exemplary compounds above, Ph represents phenyl; Cy, cyclohexyl; Bu, butyl; and Me, methyl (the same shall apply hereinafter).

The ruthenium complex represented by General Formula (2) is prepared, for example, by the method described in Inorg. synth., 1970, 12, 238 or Inorg. synth., 1977, 17, 75. To give an actual example thereof, $RuCl_3 \cdot 3H_2O$ and an excess amount of triphenylphosphine are heated under reflux in methanol to give $RuCl_2(PPh_3)_3$. Alternatively, heating of $RuCl_3 \cdot 3H_2O$, triphenylphosphine and $NaBH_4$ or heating of $RuCl_2(PPh_3)_3$, triphenylphosphine and $NaBH_4$ under reflux in ethanol gives $RuH_2(PPh_3)_4$.

When the catalyst according to the invention includes the ruthenium complex represented by General Formula (2) and a component (iii) amine, the amine is preferably a bidentate amines, more preferably an ethylenediamine skeleton-containing diamine containing an ethylene group as $Q^2$ in General Formula (6), such as ethylenediamine or (1R,2R)-1,2-diphenylethylenediamine.

Further, as in the aspect (a) of the invention, the components (i), (ii) and (iii) may be present independently as a mixture (catalyst E). In such a case, the ruthenium compound, the monodentate monophosphine or bisphosphine, and the amine described above are favorably used respectively as the components (i), (ii) and (iii).

The method for producing alcohols according to the invention can be carried out favorably in the presence or absence of a solvent, and use of a solvent is preferable. The solvent for use is preferably a solvent dissolving the hydrogenation substrate and the catalyst ruthenium complex, and may be a single solvent or a mixed solvent. Typical examples thereof include aromatic hydrocarbons such as toluene and xylene, aliphatic hydrocarbons such as hexane and heptane, halogenated hydrocarbons such as methylene chloride and chlorobenzene, ethers such as diethyl ether, tetrahydrofuran, methyl t-butyl ether and cyclopentyl methyl ether, alcohols such as methanol, ethanol, isopropanol, n-butanol and 2-butanol, polyvalent alcohols such as ethylene glycol, propylene glycol, 1,2-propanediol and glycerol, nitriles such as acetonitrile, amides such as N,N-dimethylformamide and N-methylpyrrolidone; and amines such as pyridine and triethylamine. Among them, ethers are preferred. Particularly preferable is tetrahydrofuran. The amount of the solvent used may be altered properly according to the reaction condition, and the amount is 0.5 mol/L to 8.0 mol/L, preferably 0.8 mol/L to 2.0 mol/L, with respect to the substrates. The reaction is carried out under agitation as needed.

In the method for producing alcohols by using a catalyst according to the invention, the reaction may be carried out with additives added as needed to the reaction system. In a favorable embodiment of the invention, a base may be used as the additive. Addition of the base to the reaction system, i.e., reaction in the presence of a base, assures smooth progress of hydrogen reduction. The base to be added to the reaction system is, for example, an organic or inorganic base compound.

Typical examples of the organic base compounds for use in the invention include amines such as triethylamine, diisopropylethylamine, N,N-dimethylaniline, piperidine, pyridine, 4-dimethylaminopyridine, 1,5-diazabicyclo[4,3,0]nona-5-ene, 1,8-diazabicyclo[5,4,0]undeca-7-ene, tri-n-butylamine and N-methylmorpholine. Particularly preferred among them are triethylamine, diisopropylethylamine, and the like.

Other examples of the organic base compounds include the following phosphazene compounds.

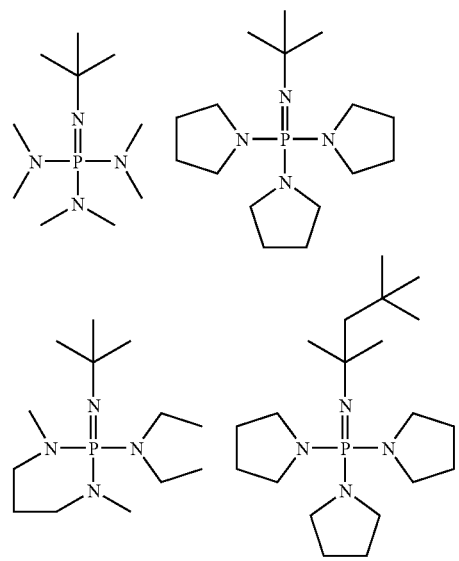

-continued

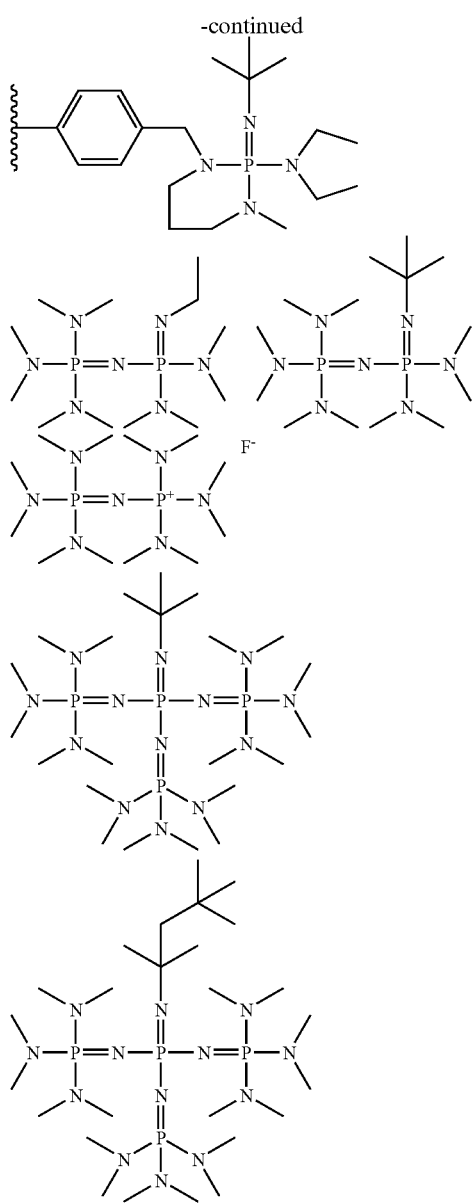

Examples of the inorganic base compounds for use in the invention include alkali metal carbonates such as potassium carbonate, sodium carbonate, lithium carbonate, and cesium carbonate; alkali-earth metal carbonates such as magnesium carbonate and calcium carbonate; alkali metal hydroxides such as sodium hydroxide, potassium hydroxide and lithium hydroxide; alkali-earth metal hydroxides such as magnesium hydroxide and calcium hydroxide; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, and lithium tert-butoxide; alkali-earth metal alkoxides such as magnesium methoxide and magnesium ethoxide; and metal hydrides such as sodium hydride and calcium hydride. Particularly preferred among them are potassium tert-butoxide and sodium methoxide.

The amount of the base compound for use in the invention may be altered properly according to the ruthenium compound and ruthenium complex used, the reaction condition, and others. For example, the amount is normally 2 to 100,000 equivalences, preferably 5 to 10,000 equivalences with respect to the ruthenium complex. The base compound may be added, as it is or as it is dissolved, for example, in a reaction solvent, to the reaction system.

As described above, the base may be added, directly or indirectly as it is dissolved in a solution, to the reaction system containing the ruthenium complex, a hydrogenation substrate and as needed a solvent or to the reaction system containing a catalyst consisting of the ruthenium complex and an amine or of a ruthenium compound, monophosphine and an amine, a hydrogenation substrate, and as needed a solvent. Preferably, the ruthenium complex and the base are mixed previously before they are used as a catalyst. For example, when the catalyst A or B is used, the ruthenium complex and the base are mixed and agitated previously in a solvent, and the residue after solvent vaporization is added to the reaction system or alternatively, a solution of the residue redissolved in a solvent is added as a catalyst to the reaction system. When the catalyst C, D or E isused, the catalyst consisting of the ruthenium complex, the catalyst consisting of the ruthenium complex and the amine, or the catalyst consisting of the ruthenium compound, the monophosphine compound and the amine compound may be mixed previously with a base, before it is used as the catalyst. Specifically, the catalyst is previously mixed and agitated with the base in a solvent and the mixture solution is added as it is to the reaction system; the residue after solvent vaporization is added as a catalyst to the reaction system; or the residue is redissolved in a reaction solvent, and the solution obtained is added as a catalyst to the reaction system. In these ways, it is possible to improve the conversion rate of the hydrogenation substrate to alcohol and the selectivity, i.e., conversion rate to a desirable alcohol.

A reducing agent may also be used as needed as an additive in the invention. The reducing agent for use in the invention include Zn, $Zn(BH_4)_2$, $LiAlH_4$, $LiAlH(OBu\text{-}t)_3$, $NaAlH_4$, $LiAlHEt_3$, $(i\text{-}Bu)_2AlH$, and $NaBH_4$. The amount of the reducing agent is selected properly according to the ruthenium compound and ruthenium complex used, the reaction condition and others, and the amount is normally 1 to 50 equivalences, preferably 1 to 10 equivalences with respect to the ruthenium compound or the ruthenium complex. The reducing agent may be added as it is or as it is dissolved, for example, in the reaction solvent to the reaction system.

The reaction temperature for hydrogenation in the invention is preferably 10° C. to 200° C., more preferably 60° C. to 120° C. Unfavorably, excessively lower reaction temperature may leave much substrates unreacted, while excessively higher reaction temperature may cause decomposition of the substrates, catalyst and others.

The hydrogen pressure during hydrogenation in the invention is preferably 0.5 to 10 MPa, more preferably 3 to 6 MPa.

The amount of the catalyst used in the invention varies according to the substrate, reaction condition, kind of catalyst used as well as to an economical viewpoint. Normally, the molar ratio of the ruthenium metal to the substrate is normally in the range of 0.001 mol % to 10 mol %, preferably 0.01 mol % to 2 mol %.

The reaction time for sufficiently high substrate conversion rate is about 5 to 24 hours. After reaction, processing by one or more of commonly used purification methods such as extraction, filtration, crystallization, distillation, and various chromatographic methods gives a desired alcohol.

EXAMPLES

Hereinafter, the present invention will be described in details with reference to Examples, but it should be understood that the invention is not restricted by these Examples at all.

In the Examples, the conversion rate, the selectivity and the optical purity were determined by gas chromatography (GC) or high performance liquid chromatography (HPLC). The instruments and the analytical conditions are as follows:

<Conversion Rate and Selectivity>
GC: GC353B manufactured by GL Sciences Inc.
Column: TC-WAX manufactured by GL Sciences Inc. (inner diameter×length=0.25 mm×30 m, thickness=0.250 μm)
Condition: injection; 250° C., detector; 250° C. 80° C. (1 min.)–10° C./min.–250° C. (12 min.)

<Optical Purity>
GC: 5890 SERIES II plus manufactured by HEWLETT PACKARD Inc.
HPLC: SERIES 1100 manufactured by HEWLETT PACKARD Inc.

Examples 1 to 25 of Hydrogenation with Base

Substrates used in the following Examples 1 to 25 are esters or lactones shown by the following substrates A to H, and catalysts used are the ruthenium complexes 1 to 15 shown in the following catalysts 1 to 15.

Substrates

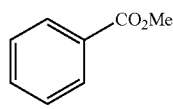
A

B

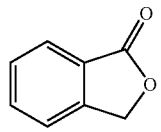
C

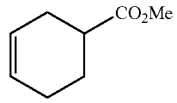
D

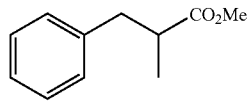
E

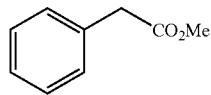
F

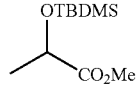
G

-continued

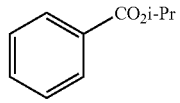
H

Catalysts
1. $RuCl_2(dppb)$ (en)
2. $RuCl_2(dppp)$ (en)
3. $RuCl_2$ (dppp) (1, 3-diaminopropane)
4. $RuCl_2(dppben)$ (en)
5. $RuCl_2(dppp)$ (dpen)
6. $RuCl_2(dppp)$ (dach)
7. $RuCl_2(dppp)$ (daipen)
8. RuCl2 (dppp) (2-aminomethylpyridine)
9. RuCl2 (dppp) (1, 3-pentanediamine)
10. $RuCl_2((S)\text{-dm-binap})$ (dpen)
11. $RuCl_2(dxpp)$ (dpen)
12. $RuCl_2((R,R)\text{-dmdppb})$ (dpen)
13. $RuCl_2(dpe)$ (dpen)
14. $RuCl_2(dppf)$ (dpen)
15. $RuCl_2((S,S)\text{-SKEWPHOS})$ (dpen)

In the aforementioned complexes, 'dppb' shows 1,4-bis (diphenylphosphino)butane, 'en' shows 1,2-ethylenediamine, 'dppp' shows 1,3-bis(diphenylphosphino)propane, 'dppben' shows 1,2-bis(diphenylphosphino)benzene, 'dpen' shows (1R,2R)-1,2-diphenylethylenediamine, 'dach' shows trans-1,2-diaminocyclohexane, 'daipen' shows 1-isopropyl-2,2-di(p-methoxyphenyl)-ethylenediamine, 'dm-binap' shows 2,2'-bis(di(3,5-xylyl)phosphino)-1,1'-binaphthyl, 'dxpp' shows 1,3-bis(di(3,5-xylyl)phosphino)propane, 'dmdppb' shows 2,3-dimethyl-1,4-bis(diphenylphosphino)-butane, 'dpe' shows 2,2'-bis(diphenylphosphino)diphenyl ether, 'dppf' shows 1,1'-bis(diphenylphosphino)ferrocene, and 'SKEWPHOS' shows 2,4-bis(diphenylphosphino)pentane.

In the Examples, the selectivity is the rate, to the total area of the GC peaks other than that of the substrate, of the GC area % of corresponding alcohol.

The ruthenium complexes of the catalysts 1 to 15 used in the Examples were synthesized by the method described in JP-A 11-189600, Example 2. Specifically, $[RuCl_2(L_P^2)]$ $(dmf)_n$ (dmf: dimethylformamide) was synthesized first according to the method described in Org. Synth., 71, 1 (1993), and then a complex of $[RuCl_2(L_P^2)(L_N^2)]$ was synthesized in reaction of $[RuCl_2(L_P^2)]$ $(dmf)_n$ with a diamine compound $(L_N^2)$. Production example of the ruthenium complex of catalyst 1 is described below as Synthesis Example 1, and the ruthenium complexes of catalysts 2 to 15 can be prepared in a similar manner to the ruthenium complex of catalyst 1.

Synthesis Example 1

Synthesis of Ruthenium Complex 1

1,4-Bis(diphenylphosphino)butane (141 mg, 0.33 mmol) and $[Ru(benzene)Cl_2]_2$ (81.7 mg, 0.16 mmol) were weighed and charged into a 20-mL Schlenk flask. The pressure in the flask was reduced to degas therefrom and then nitrogen gas was introduced into the flask. DMF (8 mL) was added thereto through a syringe; the mixture was heated in an oil bath at 120° C. under nitrogen atmosphere for 1.5 hours and then cooled to an oil bath temperature of 60° C.; and DMF was removed by vaporization under reduced pressure (1 mmHg). Dichloromethane (5 mL) and ethylenediamine (22 μL, 0.33 mmol) were added with syringe, and the mixture was heated in an oil bath at 40° C. for 1.5 hours. Dichloromethane was removed by vaporization under reduced pressure (1 mmHg), and the powder thus obtained was dried under reduced pressure (1 mmHg), to give 216 mg of a desired product (yield: 99%).

Examples 1 TO 5

The hydrogenation substrate A or C (4.0 mmol), the catalyst 1, 2, 4 or 8 (0.008 mmol), sodium methoxide (0.4 mmol), and tetrahydrofuran (3mL) were placed in a 100-ml autoclave equipped with a stirrer-bar, and the mixture was subjected to hydrogenation at a hydrogen pressure of 5 MPa at 100° C. for the period shown in the following Table 1. The results are summarized in the following Table 1.

TABLE 1

| Example No. | Reaction time (hr) | Substrate | Catalyst | Conversion rate (%) | Selectivity (%) |
|---|---|---|---|---|---|
| 1 | 3 | A | 1 | 41.5 | 65.3 |
| 2 | 3 | A | 2 | 62.8 | 78.5 |
| 3 | 3 | A | 4 | 38.2 | 58.8 |
| 4 | 18 | C | 2 | 99.5 | >99 |
| 5 | 16 | A | 8 | 43.4 | 87.1 |

Examples 6 TO 25

The catalyst 2, 3, 5, 6, 7, 9, 10, 11, 12, 13, 14 or 15, potassium t-butoxide (20 equivalences with respect to the ruthenium complex) and isopropyl alcohol (1 ml) were placed in a 20-mL Schlenk flask, and the mixture was stirred at room temperature for 20 minutes. After agitation, the isopropyl alcohol was removed by vaporization, and the residue was dissolved in tetrahydrofuran (1.33 mol/L), to give a hydrogenation catalyst solution.

Subsequently, the hydrogenation substrate A, B, D, E, F, G or H and the catalyst solution prepared were placed in a 100-ml autoclave equipped with a stirrer-bar, and the mixture was subjected to hydrogenation at a hydrogen pressure of 5 MPa at 100° C. The hydrogenation results are summarized in the following Table 2.

TABLE 2

| Example No. | Reaction time (hr) | Substrate (mmol) | Catalyst (mmol) | Conversion rate (%) | Selectivity (%) |
|---|---|---|---|---|---|
| 6 | 8 | A (4.0) | 2 (0.008) | 88.7 | 92.2 |
| 7 | 8 | A (4.0) | 3 (0.008) | 89.5 | 92.9 |
| 8 | 8 | B (4.0) | 2 (0.008) | 70.5 | 61.7 |
| 9 | 8 | A (4.0) | 5 (0.008) | 100 | 97.7 |
| 10 | 19 | A (4.0) | 7 (0.008) | 73.0 | 82.1 |
| 11 | 15 | A (4.0) | 6 (0.008) | 99.8 | 97.8 |
| 12 | 16 | B (4.0) | 5 (0.008) | 98.0 | 94.8 |
| 13 | 15 | D (3.6) | 2 (0.007) | 91.3 | 28.5 |
| 14* | 21 | A (40.0) | 5 (0.02) | 91.5 | 97.2 |
| 15 | 16 | E (2.8) | 5 (0.014) | 99.8 | 91.3 |
| 16 | 15 | F (3.3) | 5 (0.017) | 100 | 98.7 |
| 17 | 15 | E (2.8) | 9 (0.014) | 90.1 | 76.3 |
| 18 | 15 | A (4.0) | 10 (0.02) | 99.3 | 95.8 |
| 19 | 15.5 | E (2.8) | 11 (0.014) | 100 | 98.6 |
| 20*** | 14 | E (2.8) | 12 (0.035) | 97.6 | 95.8 |
| 21*** | 16.5 | G (2.1) | 5 (0.014) | 99.9 | 29.2(2-Si) 69.6(1-Si) |
| 22* | 22 | H (30.7) | 5 (0.015) | 74.8 | 73.4 |
| 23** | 16 | A (4.0) | 13 (0.004) | 24.4 | 34.6 |
| 24** | 15 | A (4.0) | 14 (0.004) | 71.5 | 74.6 |
| 25 | 5 | A (4.0) | 15 (0.008) | 92.7 | 96.7 |

In the above Table 2, (2-Si) shows 2-O-silylated diol, (1-si) shows 1-O-silylated diol.
*reaction at 70° C.
**reaction at 80° C.
***The amount of potassium t-butoxide is 0.1 equivalences with respect to the hydrogenation substrates.

Examples 26 TO 32 of Hydrogenation in the Presence of $BH_4$ Type-Catalyst

The catalysts used in the following Examples 26 to 32 are the ruthenium complexes 16 to 18 described in the following Synthesis Examples 2 to 4.

Synthesis Example 2

1,3-Bis(diphenylphosphino)propane (dppp) (680 mg, 1.65 mmol) and [Ru(benzene)$Cl_2$]$_2$ (408.2 mg, 0.816 mmol) were weighed and charged into a 100-mL Schlenk flask and then the gas in the flask was substituted with nitrogen gas. DMF (30 mL) was added thereto under nitrogen atmosphere; the mixture was heated in an oil bath at 120° C. under nitrogen atmosphere for 4.0 hours and then cooled to an oil bath temperature of 60° C.; and DMF was removed by vaporization under reduced pressure (1 mmHg). Dichloromethane (25mL) and 1,2-diphenylethylenediamine (dpen) (350 mg, 1.65 mmol) were added thereto, and the mixture was heated in an oil bath at 40° C. for 2.0 hours. Dichloromethane was removed by vaporization under reduced pressure (1 mmHg), and $NaBH_4$ (1.56 g, 41.2 mmol), toluene (15 mL) and ethanol (15 mL) were added thereto. The mixture was heated in an oil bath at 65° C. for 5 minutes and then, stirred at room temperature for 30 minutes.

The reaction solution was Celite-filtered, and the filtrate was evaporated under reduced pressure (1 mmHg). Toluene (50 mL) was added to the residue obtained, and the mixture was stirred for 30 minutes while heated in an oil bath at 40° C. The reaction solution was Celite-filtered, and the filtrate was evaporated under reduced pressure (1 mmHg), to give a powder. The powder obtained was further dried under reduced pressure (1 mmHg), to give 1.1 g of RuH($\eta^1$-BH$_4$) (dppp) (dpen) (Complex 16). Yield was 90%.

Synthesis Example 3

RuH($\eta^1$-BH$_4$) (dppp) (en) (Complex 17) was prepared in a similar manner to Synthesis Example 2, except that 1,2-diphenylethylenediamine (dpen) used in Synthesis Example 2 was replaced with ethylenediamine (en).

Synthesis Example 4

RuH($\eta^1$-BH$_4$) (dppb) (dpen) (Complex 18) was prepared in a similar manner to Synthesis Example 2, except that 1,3-bis (diphenylphosphino) propane (dppp) in Synthesis Example 2 was replaced with 1,4-bis(diphenylphosphino) butane (dppb).

Example 26

Methyl benzoate (4.0 mmol), Complex 16 (0.008 mmol) obtained in Synthesis Example 2, and tetrahydrofuran (3 mL) were placed in a 100-ml autoclave equipped with a stirrer-bar, and the mixture was subjected hydrogenation at a hydrogen pressure of 5 MPa at 100° C. for 8 hours. The hydrogenation gave benzyl alcohol at a conversion rate of 97.4% and a selectivity of 100%.

Example 27

Methyl 3-methoxypropionate (4.27 mmol), Complex 16 (0.021 mmol) obtained in Synthesis Example 2, and tetrahydrofuran (1 mL) were placed in an autoclave equipped with a stirrer-bar, and the mixture was subjected hydrogenation at a hydrogen pressure of 5 MPa at 80° C. for 16 hours. The hydrogenation gave 3-methoxypropanol at a conversion rate of 79.8% and a selectivity of 94.1%.

Example 28

Methyl (S)-3-(t-butyldimethylsilyloxy)butyrate (2.0 mmol, optical purity 98.8% ee), Complex 16 (0.01 mmol) obtained in Synthesis Example 2, and tetrahydrofuran (0.5 mL) were placed in a 100-ml autoclave equipped with a rotator, and the mixture was subjected to hydrogenation at a hydrogen pressure of 5 MPa at 80° C. for 16 hours. The hydrogenation gave (S)-3-(t-butyldimethylsilyloxy)-1-butanol at a conversion rate of 100% and a selectivity of 98.8%. The optical purity of the alcohol obtained was found to be 98.8% ee, indicating no loss in optical purity by the hydrogenation. The optical purity was determined after acetylation of the alcohol obtained.

Conversion Rate/Selectivity Analysis Condition:
  Injection temperature: 250° C.,
  Detection temperature: 250° C.
  Oven temperature: 80° C. (1 min.)–10° C./min.–250° C. (12 min.)
Optical Purity Analysis Condition:
  Injection temperature: 250° C.
  Detection temperature: 250° C.
  Oven temperature: 100° C. constant (column: CHIRASIL-DEX CB)

Example 29

Methyl (S)-2-(t-butyldimethylsilyloxy)propionate (2.1 mmol, optical purity 97.0% ee), Complex 16 (0.01 mmol) obtained in Synthesis Example 2, and tetrahydrofuran (1.0 mL) were placed in a 100-ml autoclave equipped with a stirrer-bar, and the mixture was subjected to hydrogenation at a hydrogen pressure of 5 MPa at 80° C. for 16 hours. The hydrogenation showed a conversion rate of 100%, and a selectivity of 30.4% to (S)-2-(t-butyldimethylsilyloxy)-1-propanol and a selectivity of 69.0% to (S)-1-(t-butyldimethylsilyloxy)-2-propanol. The optical purity of each of the alcohols obtained was found to be 97.0% ee, indicating no loss in optical purity by the hydrogenation.

Conversion Rate/Selectivity Analysis Condition:
  Injection temperature: 250° C.
  Detection temperature: 250° C.
  Oven temperature: 60° C. (1 min.)–10° C./min.–250° C. (10 min.)
Optical Purity Analysis Condition:
  Injection temperature: 250° C.
  Detection temperature: 250° C.
  Oven temperature: 100° C. constant (column: CHIRASIL-DEX CB)

Example 30

Methyl (S)-3-(phenylamino)butyrate (2.8 mmol, optical purity 93.9% ee), Complex 16 (0.014 mmol) obtained in Synthesis Example 2 and tetrahydrofuran (1 mL) were placed in a 100-ml autoclave equipped with a stirrer-bar, and the mixture was subjected to hydrogenation at a hydrogen pressure of 5 MPa at 100° C. for 16 hours. The hydrogenated gave (S)-3-phenylamino-1-butanol at a conversion rate of 100% and a selectivity of 99.8%. The optical purity of the (S)-3-phenylamino-1-butanol obtained was found to be 93.9% ee, indicating no loss in optical purity by the hydrogenation. The optical purity was measured after acetylation of the alcohol obtained.

Conversion Rate/Selectivity Analysis Condition:
  Injection temperature: 250° C.
  Detection temperature: 250° C.
  Oven temperature: 80° C. (1 min.)–10° C./min.–250° C. (12 min.)
Optical Purity Analysis Condition:
  Column: CHIRALCEL OJ-H
  Eluant: hexane/2-propanol=90/10
  Flow rate: 0.5 mL/minute
  Column temperature: 30° C.
  UV: 254 nm Example 31

(S)-3-(t-Butyldimethylsilyloxy)-1-butanol was prepared in a similar manner to Example 29, except that Complex 16 (0.01 mmol) used in Example 29 above was replaced with RuH($\eta^1$-BH$_4$) (dppp) (en) (complex 17) (0.02 mmol) (1 mol %) prepared in Synthesis Example 3.

Hydrogenation gave the desired alcohol at a conversion rate of 96.7% and a selectivity of 94.7%, and there was no loss in optical purity by the hydrogenation.

Example 32

(S)-3-(t-Butyldimethylsilyloxy)-1-butanol was prepared in a similar manner to Example 29, except that the complex 16 (0.01 mmol) used in Example 29 above was replaced with RuH($\eta^1$-BH$_4$) (dppb) (en) (Complex 18) (0.02 mmol) (1 mol %) prepared in Synthesis Example 4.

Hydrogenation gave the desired alcohol at a conversion rate of 100% and a selectivity of 98.8%, and there was no loss in optical purity by the hydrogenation.

Example 33

Methyl (S)-3-(t-butoxycarbonylamino)butyrate (2.3 mmol, optical purity >99% ee), Complex 16 (0.023 mmol) obtained in Synthesis Example 2 and tetrahydrofuran (1 mL) were placed in a 100-ml autoclave equipped with a stirrer-bar, and the mixture was subjected to hydrogenation at a hydrogen pressure of 5 MPa at 100° C. for 17 hours. The hydrogenated gave (S)-3-(t-butoxycarbonylamino)-1-butanol at a conversion rate of 99.4% and a selectivity of 98.8%. The optical purity of the (S)-3-(t-butoxycarbonylamino)-1-butanol obtained was found to be up to 99.0% ee, indicating no loss in optical purity by the hydrogenation. The optical purity was measured after p-nitrobenzoylation of the alcohol obtained.

Optical Purity Analysis Condition:
Column: CHIRALPAK AD
Eluant: hexane/2-propanol=90/10
Flow rate: 1.0 mL/minute
Column temperature: 40° C.
UV: 254 nm Example 34

Methyl (S)-2-(t-butoxycarbonylamino)propionate (2.46 mmol, optical purity>99.0%ee), Complex 16 (0.246 mmol) obtained in Synthesis Example 2 and tetrahydrofuran (1 mL) were placed in a 100-ml autoclave equipped with a stirrer-bar, and the mixture was subjected to hydrogenation at a hydrogen pressure of 5 MPa at 80° C. for 16 hours. The hydrogenated gave (S)-2-(t-butoxycarbonylamino)-1-propanol at a conversion rate of 100% and a selectivity of 98.9%. The optical purity of the (S)-2-(t-butoxycarbonylamino)-1-propanol obtained was found to be 99.0% ee, indicating no loss in optical purity by the hydrogenation. The optical purity was measured after p-nitrobenzoylation of the alcohol obtained.

Optical Purity Analysis Condition:
Column: CHIRALCEL OD
Eluant: hexane/2-propanol=95/5
Flow rate: 1.0 mL/minute
Column temperature: 40° C.
UV: 254 nm Example 35

Methyl (S) -lactate (5.0 mmol, optical purity 99.6% ee), Complex 16 (0.05 mmol) obtained in Synthesis Example 2 and tetrahydrofuran (2 mL) were placed in a 100-ml autoclave equipped with a stirrer-bar, and the mixture was subjected to hydrogenation at a hydrogen pressure of 5 MPa at 80° C. for 17 hours. The hydrogenated gave (S)-1,2-propanediol at a conversion rate of 62.0% and a selectivity of 96.8%. The optical purity of the alcohol obtained was found to be 92.5% ee, and an alcohol obtained retains an optical purity of 90% or more of that of the ester in optical purity. The optical purity was measured after carbonation of the alcohol obtained.

Optical Purity Analysis Condition:
Column: β-DEX 225
Injection temperature: 250° C.
Detection temperature: 250° C.
Oven temperature: 170° C. constant Example 36 AND 37 of Hydrogenation with Base Synthesis Example 5

Synthesis of RuCl$_2$[PPh$_3$]$_2$[(1R,2R)-1,2-diphenylethylenediamine]; Complex 19

RuCl$_2$(PPh$_3$)$_3$ (800 mg, 0.83 mmol) and (1R,2R)-1,2-diphenyl-ethylenediamine (195 mg, 0.92 mmol) are weighed and charged into a 20-mL Schlenk flask. The flask was reduced pressure to degas therein and then nitrogen gas was introduced into the flask. Dichloromethane (8 mL) was added thereto through a syringe, and the mixture was stirred under nitrogen atmosphere at room temperature for 3 hours. The reaction solution was then Celite-filtered, and the Celite layer was washed with dichloromethane (2mL). The filtrate obtained was concentrated under reduced pressure to a volume of about 2 mL; hexane (16 mL) was added thereto; and the mixture was stirred at room temperature for 1 hour. The precipitate was collected by filtration under nitrogen atmosphere, and the powder obtained was dried under reduced pressure (1 mmHg), to give 531 mg of a desired product (yield: 70%).

Example 36

Hydrogenation of Methyl Benzoate

Complex 19 (0.02 mmol) obtained in Synthesis Example 5 and potassium t-butoxide (0.4 mmol) were weighed and charged into a 100-ml autoclave equipped with a stirrer-bar; tetrahydrofuran (3mL) and methyl benzoate (4.0 mmol) were added thereto through a syringe; and the mixture was stirred at a hydrogen pressure of 5 MPa at 100° C. for 15 hours. As a result, the conversion rate of methyl benzoate was 88.9%, and the selectivity to benzyl alcohol was 93.2%.

Example 37

Reduction of Phthalide

Phthalide (3.73 mmol), Complex 19 (0.0373 mmol) obtained in Synthesis Example 5 and potassium t-butoxide (0.373 mmol) were weighed and charged into a 100-ml autoclave equipped with a stirrer-bar; tetrahydrofuran (3 mL) was added thereto through a syringe; and the mixture was stirred at a hydrogen pressure of 5 MPa at 100° C. for 16 hours. As a result, the conversion rate of phthalide was 84.8%, and the selectivity to o-xylylene glycol was 97.1%.

Examples 38 to 43 of Hydrogen Reduction with Base

Example 38

Reduction of Methyl Benzoate

RuCl$_2$(PPh$_3$)$_3$ (0.02 mmol), (1R,2R)-1,2-diphenylethylene-diamine (0.02 mmol) and potassium t-butoxide (0.4 mmol) were weighed and charged into a 100-ml autoclave equipped with a stirrer-bar; tetrahydrofuran (3 mL) and methyl benzoate (4.0 mmol) were added thereto through a syringe; and the mixture was stirred at a hydrogen pressure of 5 MPa at 100° C. for 15 hours. As a result, the conversion rate of methyl benzoate was 81.7%, and the selectivity to benzyl alcohol was 89.0%.

Example 39

Reduction of Methyl Hexanoate

RuCl$_2$(PPh$_3$)$_3$ (0.017mmol), (1R,2R)-1,2-diphenylethylene-diamine (0.017 mmol) and potassium t-butoxide (0.34 mmol) were weighed and charged into a 100-ml autoclave equipped with a stirrer-bar; tetrahydrofuran (3 mL) and methyl hexanoate (3.4 mmol) were added thereto through a syringe; and the mixture was stirred at a hydrogen pressure of 5 MPa at 100° C. for 15 hours. As a result, the conversion rate of methyl hexanoate was 48.7%, and the selectivity to 1-hexanol was 43.1%.

Example 40

Reduction of Methyl Benzoate

RuCl$_2$(PPh$_3$)$_3$ (0.02 mmol) and potassium t-butoxide (0.4 mmol) were weighed and charged into a 100-ml autoclave equipped with a stirrer-bar; ethylenediamine (0.02 mmol), tetrahydrofuran (3 mL), and methyl benzoate (4.0 mmol) were added thereto through a syringe; and the mixture was stirred at a hydrogen pressure of 5 MPa at 100° C. for 15 hours. As a result, the conversion rate of methyl benzoate was 18.0%, and the selectivity to benzyl alcohol was 35.3%.

Example 41

Reduction of Methyl Benzoate

RuCl$_2$(PPh$_3$)$_3$ (0.02 mmol) and potassium t-butoxide (0.4 mmol) were weighed and charged into a 100-ml autoclave equipped with a stirrer-bar; trans-1,2-diaminocyclohexane (0.02 mmol), tetrahydrofuran (3 mL) and methyl benzoate (4.0 mmol) were added thereto through a syringe; and the mixture was stirred at a hydrogen pressure of 5 MPa at 100° C. for 15 hours. As a result, the conversion rate of methyl benzoate was 26.6%, and the selectivity to benzyl alcohol was 52.5%.

Synthesis Example 6

Preparation of RuCl$_2$ (PMe$_3$)$_2$(ethylenediamine); Complex 20

(cod)Ru($\eta^3$-methallyl)$_2$ (150 mg, 0.47 mmol) was weighed and charged into a 100-ml autoclave equipped with a stirrer-bar; heptane (3 mL) and 1.0 M PMe$_3$ toluene solution (1 mL, 1.0 mmol) were added thereto through a syringe under nitrogen atmosphere; and the mixture was stirred at 80° C. for 5 hours. The reaction solution was transferred into a 20-mL Schlenk flask; the solvent was removed by distillation under reduced pressure; and the powder obtained was dried under reduced pressure, to give 132 mg of (PMe$_3$)$_2$ Ru($\eta^3$-methallyl)$_2$ (yield: 77%).

The (PMe$_3$)$_2$Ru($\eta^3$-methallyl)$_2$ (123.6 mg, 0.34 mmol) thus obtained was weighed and charged into a 20-mL Schlenk flask; acetone (3 mL) and 1.25 M HCl ethanol solution (0.6 mL, 0.75 mmol) were added thereto through a syringe under nitrogen atmosphere; and the mixture was stirred at room temperature for 2 hours. The solvent was removed by vaporization under reduced pressure; dimethylformamide (3 mL) and ethylenediamine (60 μL, 0.90 mmol) were added thereto through a syringe, and the mixture was stirred at room temperature for 3 hours. The solvent was removed by vaporization under reduced pressure, and the powder obtained was dried under reduced pressure, to give 123 mg of a desired product (yield: 94%).

Example 42

Reduction of Methyl Benzoate

Complex 20 (0.02 mmol) obtained in Synthesis Example 6 and potassium t-butoxide (0.4 mmol) were weighed and charged into a 100-ml autoclave equipped with a stirrer-bar; tetrahydrofuran (3 mL) and methyl benzoate (4.0 mmol) were added thereto through a syringe; and the mixture was stirred at a hydrogen pressure of 5 MPa at 100° C. for 15 hours. As a result, the conversion rate of methyl benzoate was 49.0%, and the selectivity to benzyl alcohol was 76.1%.

Synthesis Example 7

Preparation of RuCl$_2$[PMe$_3$]$_2$[(1R,2R)-1,2-diphenyl-ethylenediamine]; Complex 21

(cod)Ru($\eta^3$-methallyl)$_2$ (150 mg, 0.47 mmol) was weighed and charged into a 100-ml autoclave equipped with a stirrer-bar; heptane (3 mL) and 1.0 M PMe$_3$ toluene solution (1 mL, 1.0 mmol) were added thereto through a syringe under nitrogen atmosphere; and the mixture was stirred at 80° C. for 6.5 hours. The reaction solution was transferred into a 20-mL Schlenk flask; the solvent was removed by vaporization under reduced pressure; and the powder obtained was dried under reduced pressure, to give 144 mg of (PMe$_3$)$_2$Ru($\eta^3$-methallyl)$_2$ (yield: 84%). Then, acetone (3 mL) and 1.25 M HCl ethanol solution (0.7 mL, 0.88 mmol) were added thereto through a syringe, and the mixture was stirred under nitrogen atmosphere at room temperature for 2 hours. The solvent was removed by vaporization under reduced pressure; dimethylformamide (3 mL), (1R,2R) -1,2-diphenylethylenediamine (84.1 mg, 0.40 mmol) and triethylamine (0.07 mL, 0.50 mmol) were added thereto; and the mixture was stirred at room temperature for 3 hours. The solvent was removed by vaporization under reduced pressure; toluene (4 mL) was added thereto; and the resulting mixture was stirred at room temperature for 5 minutes. The reaction solution was Celite-filtered; the filtrate was evaporated under reduced pressure; the powder obtained was dried under reduced pressure, to give 196 mg of a desired product (yield: 92%).

Example 43

Reduction of Methyl Benzoate

The complex 21 (0.02 mmol) obtained in Synthesis Example 7 and potassium t-butoxide (0.4 mmol) were weighed and charged into a 100-ml autoclave equipped with a stirrer-bar; tetrahydrofuran (3 mL) and methyl benzoate (4.0 mmol) were added thereto through a syringe; and the mixture was stirred at a hydrogen pressure of 5 MPa at 100° C. for 15 hours. As a result, the conversion rate of methyl benzoate was 55.9%, and the selectivity to benzyl alcohol was 70.1%.

INDUSTRIAL APPLICABILITY

The invention provides an industrially advantageous method of directly producing alcohols from esters or lactones at high yield and high catalytic efficiency without deterioration in optical purity at relatively low hydrogen pressure and reaction temperature, and thus, is useful in various industrial fields such as of foods, pharmaceuticals, cosmetics, and flavoring agents, particularly in production of chemical products in the chemical industry field.

What is claimed is:

1. A method for producing alcohols, comprising reducing esters or lactones with hydrogen gas in the presence of a catalyst comprising the following components (i), (ii) and (iii): (i) a ruthenium compound; (ii) a monodentate monophosphine or a bidentate bisphosphine; and (iii) an amine,
    wherein the catalyst is a catalyst comprising an amine and a ruthenium-monophosphine complex represented by the following General Formula (2): Ru $X^1X^2 (L_P^1)_r$, wherein $X^1$ and $X^2$ each represent an anionic ligand, $L_P^1$ represents a monophosphine ligand, and r is 3 or 4.

2. A method for producing alcohols, comprising reducing esters or lactones with hydrogen gas in the presence of a catalyst comprising the following components (i), (ii) and (iii): (i) a ruthenium compound; (ii) a monodentate monophosphine or a bidentate bisphosphine; and (iii) an amine,
    wherein the catalyst is a ruthenium (Ru) complex represented by the following General Formula (1): Ru $X^1X^2 (L_P)_m)L_N)_n$, wherein $X^1$ and $X^2$ each represent an anionic ligand; $L_P$ represents a phosphine ligand; m is 1 when $L_P$ is bidentata, while m is 2 when $L_P$ is monodentate; $L_N$ represents an amine ligand; and n is 1 when $L_N$ is bidentate, while n is 2 when $L_N$ is monodentate,
    wherein $L_P$ is a bisphosphine ligand and $L_N$ is a diamine ligand in the ruthenium complex represented by General Formula (1).

3. The method for producing alcohols according to claim 2, wherein $X^1$ and $X^2$ are halogen atoms in the ruthenium complex represented by General Formula (1).

4. The method for producing alcohols according to claim 2, wherein $X^1$ is a hydrogen atom, and $X^2$ is $BH_4$ in the ruthenium complex represented by General Formula (1).

5. The method for producing alcohols according to any one of claims 1 to 4, wherein the esters or lactones are reduced further in the presence of an additive or additives.

6. The method for producing alcohols according to claim 5, wherein a mixture of the ruthenium complex represented by General Formula (1) or (2) and the additive or additives previously mixed is used as the catalyst.

7. The method for producing alcohols according to claim 5, wherein the additive is a base or a reducing agent.

8. The method for producing alcohols according to claim 4, wherein an ester or lactone to be used is an optically active substance, and an alcohol obtained retains an optical purity of 90% or more of that of the ester or lactone to be hydrogen-reduced.

* * * * *

UNITED STATES PATENT AND TRADEMARK OFFICE
CERTIFICATE OF CORRECTION

| | | |
|---|---|---|
| PATENT NO. | : 7,569,735 B2 | Page 1 of 1 |
| APPLICATION NO. | : 12/076150 | |
| DATED | : August 4, 2009 | |
| INVENTOR(S) | : Yasunori Ino et al. | |

It is certified that error appears in the above-identified patent and that said Letters Patent is hereby corrected as shown below:

ON THE TITLE PAGE OF THE PATENT:

In Item "(73) Assignee", please change "Takasago International" to

--Takasago International Corporation--.

Signed and Sealed this

Twenty-second Day of June, 2010

David J. Kappos
*Director of the United States Patent and Trademark Office*